(12) United States Patent
Horner et al.

(10) Patent No.: US 6,984,213 B2
(45) Date of Patent: Jan. 10, 2006

(54) BIOPSY NEEDLE DEVICE

(75) Inventors: Shawn K. Horner, Woods Cross, UT (US); F. Mark Ferguson, Salt Lake City, UT (US); Donald D. Solomon, North Salt Lake, UT (US)

(73) Assignee: Specialized Health Products, Inc., Bountiful, UT (US)

( * ) Notice: Subject to any disclaimer, the term of this patent is extended or adjusted under 35 U.S.C. 154(b) by 82 days.

(21) Appl. No.: 10/766,369

(22) Filed: Jan. 28, 2004

(65) Prior Publication Data

US 2004/0171989 A1    Sep. 2, 2004

Related U.S. Application Data

(63) Continuation-in-part of application No. 10/739,868, filed on Dec. 18, 2003, which is a continuation-in-part of application No. 10/409,819, filed on Apr. 8, 2003, now Pat. No. 6,796,962, which is a continuation-in-part of application No. 10/322,288, filed on Dec. 17, 2002, and a continuation-in-part of application No. 10/202,201, filed on Jul. 23, 2002, now Pat. No. 6,902,546, which is a continuation-in-part of application No. 09/809,357, filed on Mar. 15, 2001, now Pat. No. 6,595,955.

(60) Provisional application No. 60/424,655, filed on Nov. 7, 2002.

(51) Int. Cl.
*A61B 10/00* (2006.01)

(52) U.S. Cl. .................................................. 600/564
(58) Field of Classification Search ................ 600/562, 600/564, 567; 604/110, 198, 162, 163, 171, 604/174, 180, 192, 197, 263, 164.01, 164.08, 604/164.04, 170.01, 170.02; 128/919
See application file for complete search history.

(56) References Cited

U.S. PATENT DOCUMENTS

| | | | |
|---|---|---|---|
| 1,436,707 A | 11/1922 | Gaschke | |
| 4,332,323 A | 6/1982 | Reenstierna | 206/365 |
| 4,373,526 A | 2/1983 | Kling | 128/215 |
| 4,762,516 A | 8/1988 | Luther | 605/164 |
| 4,790,828 A | 12/1988 | Dombrowski | 604/198 |
| 4,804,371 A | 2/1989 | Vaillancourt | 604/198 |
| 4,826,490 A | 5/1989 | Byrne | 604/198 |
| 4,832,696 A | 5/1989 | Luther | 604/164 |

(Continued)

FOREIGN PATENT DOCUMENTS

EP    0 702 972 B1    7/1995

(Continued)

*Primary Examiner*—Max F. Hindenburg
*Assistant Examiner*—Brian Szmal
(74) *Attorney, Agent, or Firm*—Paul S. Evans

(57) ABSTRACT

A medical needle shield apparatus is provided that includes a first housing configured to actuate a needle cannula. A second housing is releasably engageable with the first housing. The needle cannula is disposed for slidable movement with the second housing such that the second housing is extensible from a retracted position to an extended position to enclose a distal end of the needle cannula. The second housing includes a binding member that defines binding surfaces that form an aperture configured for slidable receipt of the needle cannula. The binding member includes a drag inducing member that engages the needle cannula during slidable receipt of the needle cannula to create a drag force. The drag force and second housing facilitate rotation of the binding member relative to a longitudinal axis of the needle cannula such that the binding surfaces engage the needle cannula to prevent slidable movement of the needle cannula.

27 Claims, 34 Drawing Sheets

U.S. PATENT DOCUMENTS

| | | | | |
|---|---|---|---|---|
| 4,834,718 A | 5/1989 | McDonald | | 604/195 |
| 4,846,811 A | 7/1989 | Vanderhoof | | 604/263 |
| 4,917,669 A | 4/1990 | Bonaldo | | 604/164 |
| 4,929,241 A | 5/1990 | Kulli | | 604/263 |
| 4,931,048 A | 6/1990 | Lopez | | 604/110 |
| 4,944,725 A | 7/1990 | McDonald | | 604/164 |
| 4,950,252 A | 8/1990 | Luther | | 604/198 |
| 4,952,207 A | 8/1990 | Lemieux | | 604/164 |
| 4,964,854 A | 10/1990 | Luther | | 604/166 |
| 4,978,344 A | 12/1990 | Dombrowski | | 604/198 |
| 4,994,041 A | 2/1991 | Dombrowski | | 604/164 |
| 5,007,901 A | 4/1991 | Shields | | 604/110 |
| 5,049,136 A | 9/1991 | Johnson | | 604/198 |
| 5,051,109 A | 9/1991 | Simon | | 604/263 |
| 5,053,017 A | 10/1991 | Chamuel | | 604/192 |
| 5,059,180 A | 10/1991 | McLees | | 604/110 |
| 5,084,023 A | 1/1992 | Lemieux | | 604/167 |
| 5,084,030 A | 1/1992 | Byrne | | 604/198 |
| 5,085,648 A | 2/1992 | Purdy | | 604/198 |
| 5,127,905 A | 7/1992 | Lemieux | | 604/164 |
| 5,135,504 A | 8/1992 | McLees | | 604/164 |
| 5,147,327 A | 9/1992 | Johnson | | 604/198 |
| 5,171,229 A | 12/1992 | McNeil | | 604/192 |
| 5,183,468 A | 2/1993 | McLees | | 604/164 |
| 5,205,829 A | 4/1993 | Lituchy | | 604/164 |
| 5,215,528 A | 6/1993 | Purdy | | 604/164 |
| 5,300,045 A | 4/1994 | Plassche | | 604/263 |
| 5,312,371 A | 5/1994 | Dombrowski | | 604/198 |
| 5,313,958 A * | 5/1994 | Bauer | | 600/567 |
| 5,322,517 A | 6/1994 | Sircom | | 604/198 |
| 5,328,482 A | 7/1994 | Sircom | | 604/164 |
| 5,334,158 A | 8/1994 | McLees | | 604/110 |
| 5,342,310 A | 8/1994 | Ueyama | | 604/110 |
| 5,344,408 A | 9/1994 | Partika | | 604/192 |
| 5,348,544 A | 9/1994 | Sweeney | | 604/192 |
| 5,411,486 A | 5/1995 | Zadini | | 604/198 |
| 5,417,659 A | 5/1995 | Gaba | | 604/110 |
| 5,419,766 A | 5/1995 | Chang | | 604/110 |
| 5,423,766 A | 6/1995 | Di Cesare | | 604/192 |
| 5,458,658 A | 10/1995 | Sircom | | 604/192 |
| 5,478,313 A | 12/1995 | White | | 604/110 |
| 5,487,733 A | 1/1996 | Caizza et al. | | 604/110 |
| 5,531,704 A | 7/1996 | Knotek | | 604/192 |
| 5,533,974 A | 7/1996 | Gaba | | 604/110 |
| 5,538,508 A | 7/1996 | Steyn | | 604/192 |
| 5,549,570 A | 8/1996 | Rogalsky | | 604/198 |
| 5,558,651 A | 9/1996 | Crawford | | 604/263 |
| 5,562,624 A | 10/1996 | Righi | | 604/110 |
| 5,562,633 A | 10/1996 | Wozencroft | | 604/171 |
| 5,582,597 A | 12/1996 | Brimhall et al. | | 604/192 |
| 5,584,809 A | 12/1996 | Gaba | | 604/110 |
| 5,584,810 A | 12/1996 | Brimhall | | 604/110 |
| 5,584,818 A | 12/1996 | Morrison | | 604/197 |
| 5,599,310 A | 2/1997 | Bogert | | 604/110 |
| 5,601,532 A | 2/1997 | Gaba | | 604/110 |
| 5,601,536 A | 2/1997 | Crawford | | 604/263 |
| 5,611,781 A | 3/1997 | Sircom | | 604/164 |
| 5,662,610 A | 9/1997 | Sircom | | 604/110 |
| 5,683,365 A | 11/1997 | Brown | | 604/110 |
| 5,697,907 A | 12/1997 | Gaba | | 604/110 |
| 5,718,688 A | 2/1998 | Wozencroft | | 604/164 |
| 5,725,504 A | 3/1998 | Collins | | 604/165 |
| 5,749,856 A | 5/1998 | Zadini | | 604/162 |
| 5,853,393 A | 12/1998 | Bogert | | 604/165 |
| 5,879,337 A | 3/1999 | Kuracina | | 604/192 |
| 5,882,337 A | 3/1999 | Bogert | | 604/110 |
| 5,910,130 A | 6/1999 | Caizza et al. | | 604/110 |
| 5,911,705 A | 6/1999 | Howell | | 604/110 |
| 5,951,515 A | 9/1999 | Osterlind | | 604/110 |
| 5,980,488 A | 11/1999 | Thorne | | 604/110 |
| 6,001,080 A | 12/1999 | Kuracina | | 604/171 |
| 6,004,294 A | 12/1999 | Brimhall | | 604/164 |
| 6,117,108 A | 9/2000 | Woehr | | 604/110 |
| 6,132,401 A | 10/2000 | Van Der Meyden | | 604/195 |
| 6,193,964 B1 | 2/2001 | Shiang et al. | | 604/192 |
| 6,203,527 B1 | 3/2001 | Zadini | | 604/110 |
| 6,210,373 B1 | 4/2001 | Allmon | | 604/192 |
| 6,221,047 B1 | 4/2001 | Green et al. | | 604/164 |
| 6,280,419 B1 | 8/2001 | Vojtasek | | 604/192 |
| 6,287,278 B1 | 9/2001 | Woehr et al. | | 604/110 |
| 6,406,459 B1 | 6/2002 | Allmon | | 604/192 |
| 6,443,927 B1 | 9/2002 | Cook | | 604/110 |
| 6,443,929 B1 | 9/2002 | Kuracina et al. | | 604/192 |
| 6,585,704 B2 | 7/2003 | Luther et al. | | 604/263 |
| 6,616,630 B1 | 9/2003 | Woehr et al. | | 604/110 |
| 6,623,458 B2 | 9/2003 | Woehr et al. | | 604/192 |
| 6,629,959 B2 | 10/2003 | Kuracina et al. | | 604/192 |
| 6,652,486 B2 | 11/2003 | Bialecki et al. | | 604/110 |
| 6,682,510 B2 | 1/2004 | Niermann | | 604/263 |
| 2002/0099339 A1 | 7/2002 | Niermann | | 604/263 |
| 2002/0107483 A1 | 8/2002 | Cook | | 604/164.01 |
| 2002/0177813 A1 | 11/2002 | Adams et al. | | 604/164.07 |
| 2002/0177818 A1 | 11/2002 | Vaillancourt | | 604/198 |
| 2003/0036731 A1 | 2/2003 | Wilkinson et al. | | 604/198 |
| 2003/0114797 A1 | 6/2003 | Vaillancourt et al. | | 604/171 |
| 2003/0135157 A1 | 7/2003 | Saulenas et al. | | 604/110 |
| 2003/0144627 A1 | 7/2003 | Woehr et al. | | 604/110 |
| 2003/0195471 A1 | 10/2003 | Woehr et al. | | 604/164.08 |
| 2003/0195479 A1 | 10/2003 | Kuracina et al. | | 604/263 |
| 2003/0216687 A1 | 11/2003 | Hwang | | 604/110 |
| 2004/0010227 A1 | 1/2004 | Riesenberger et al. | | 604/110 |
| 2004/0049155 A1 | 3/2004 | Schramm | | 604/110 |

FOREIGN PATENT DOCUMENTS

| | | |
|---|---|---|
| EP | 0 750 915 A2 | 1/1997 |
| EP | 1 027 903 A1 | 8/2000 |
| EP | 1 110 571 A1 | 6/2001 |
| EP | 1 112 754 A1 | 7/2001 |
| EP | 1 374 772 A1 | 1/2004 |
| WO | WO 97/42989 | 11/1997 |
| WO | WO 01/10488 A1 | 2/2001 |
| WO | WO 01/56642 | 8/2001 |
| WO | WO 02/45786 A2 | 6/2002 |
| WO | WO 03/103757 A1 | 12/2003 |

\* cited by examiner

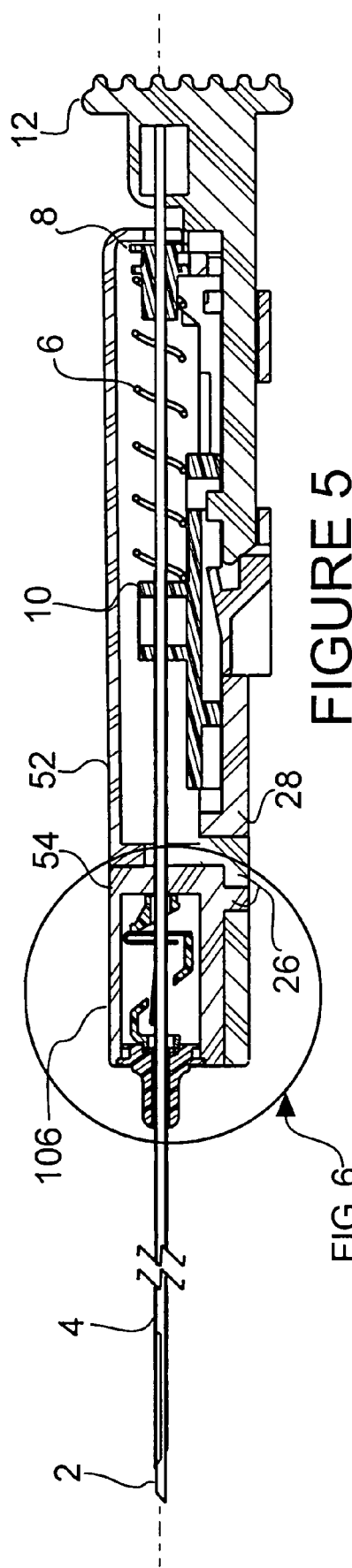
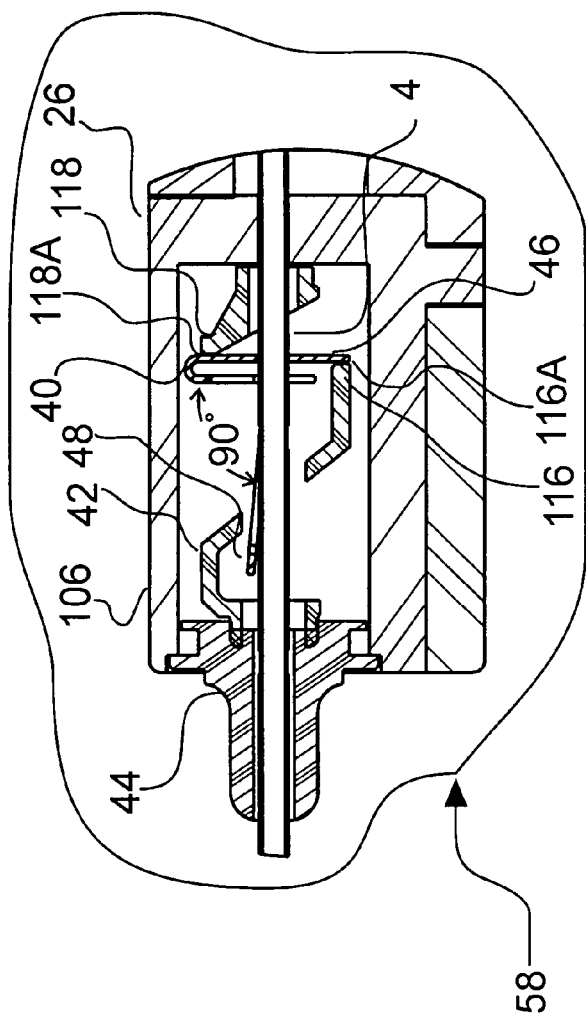

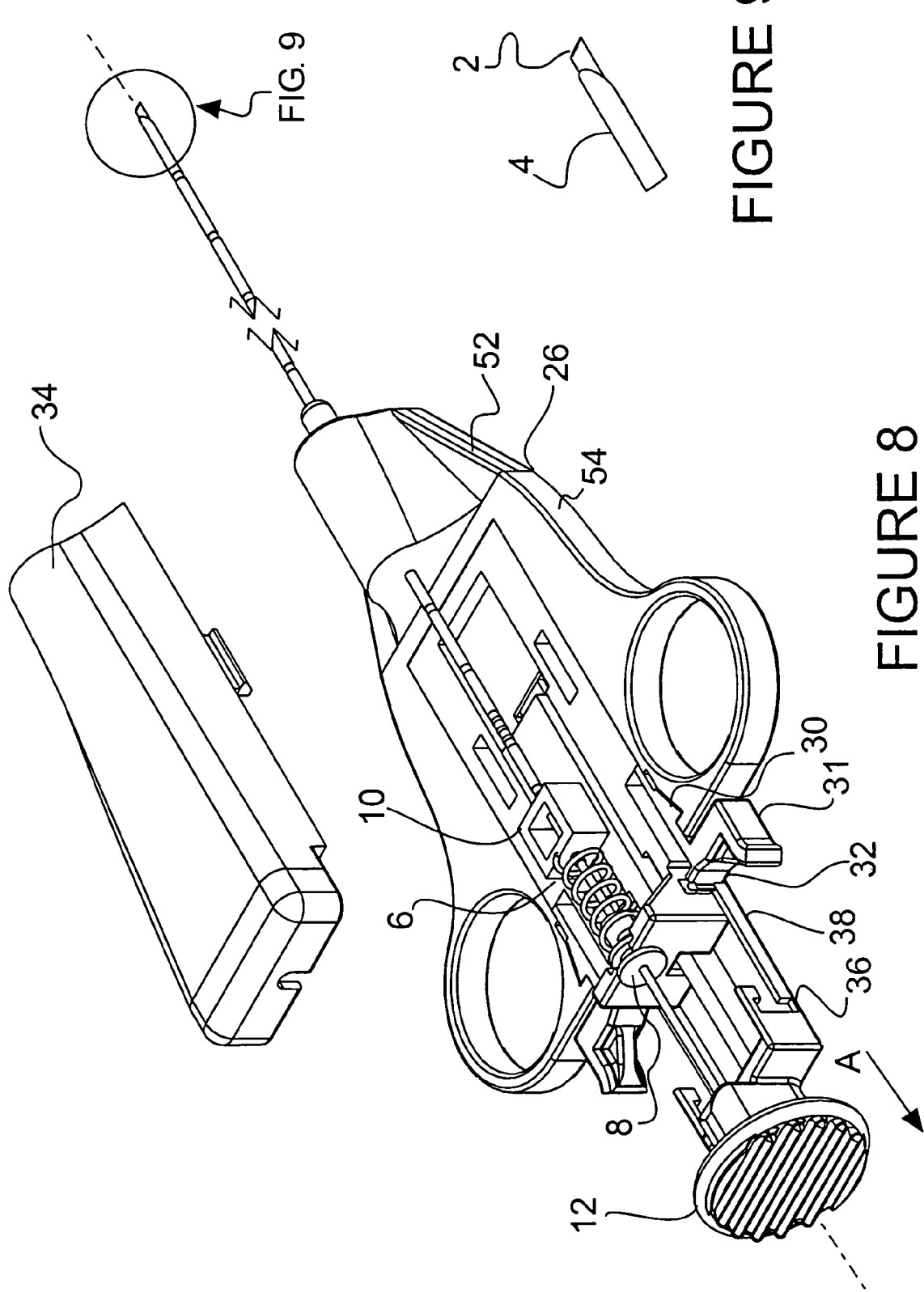

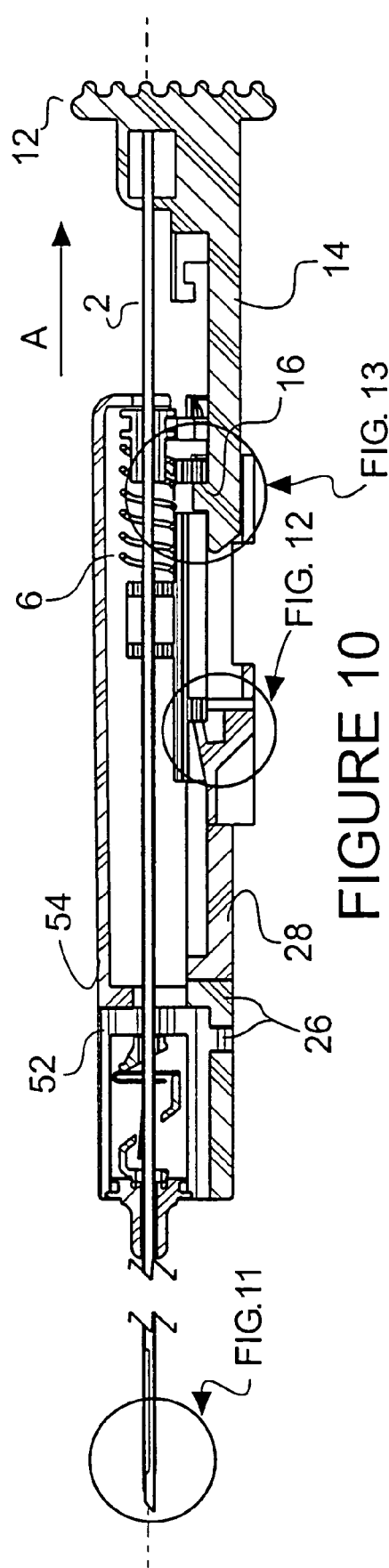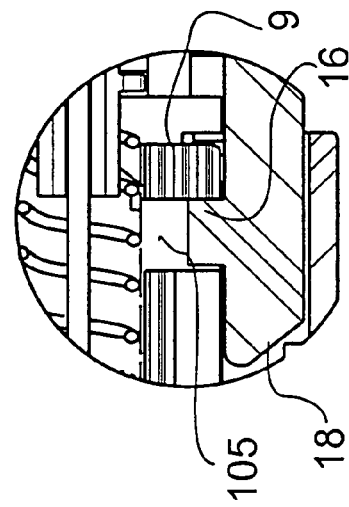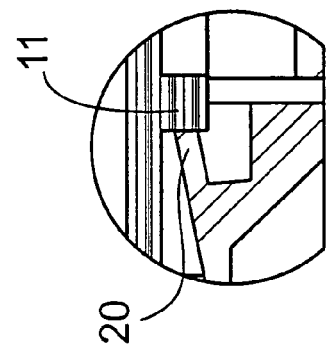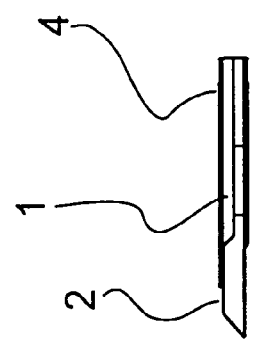
FIGURE 10
FIGURE 13
FIGURE 12
FIGURE 11

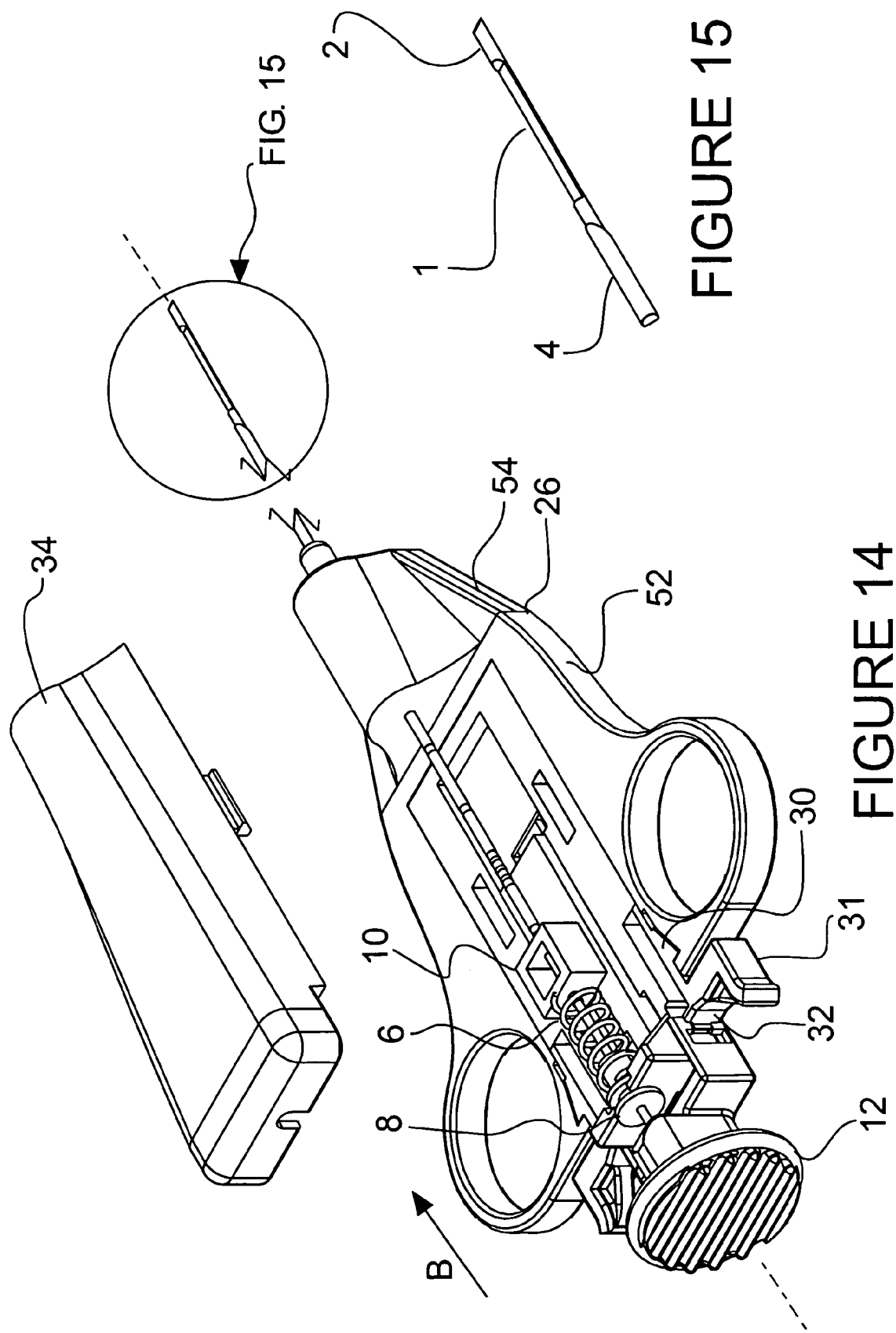

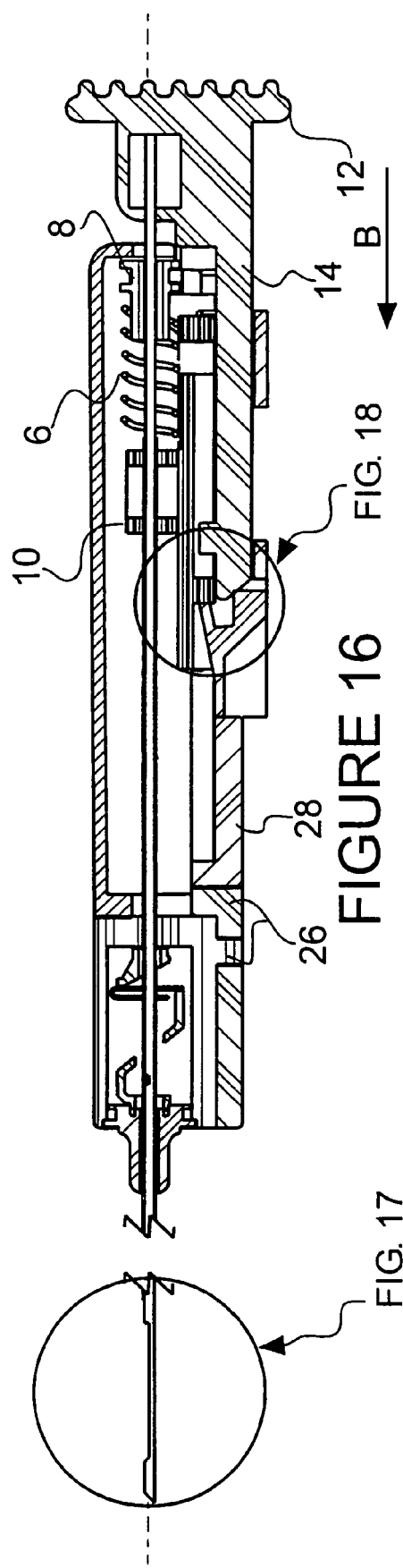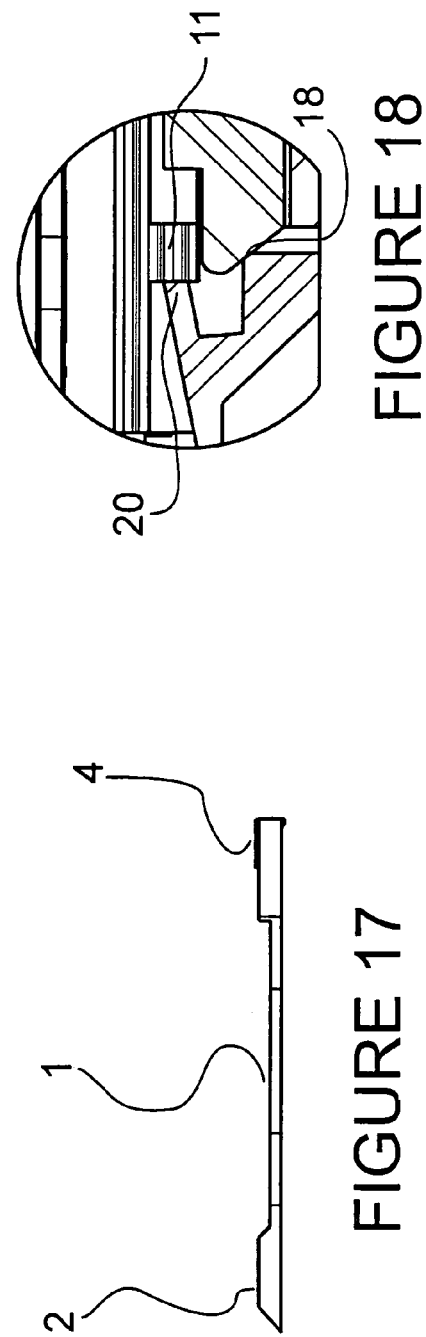

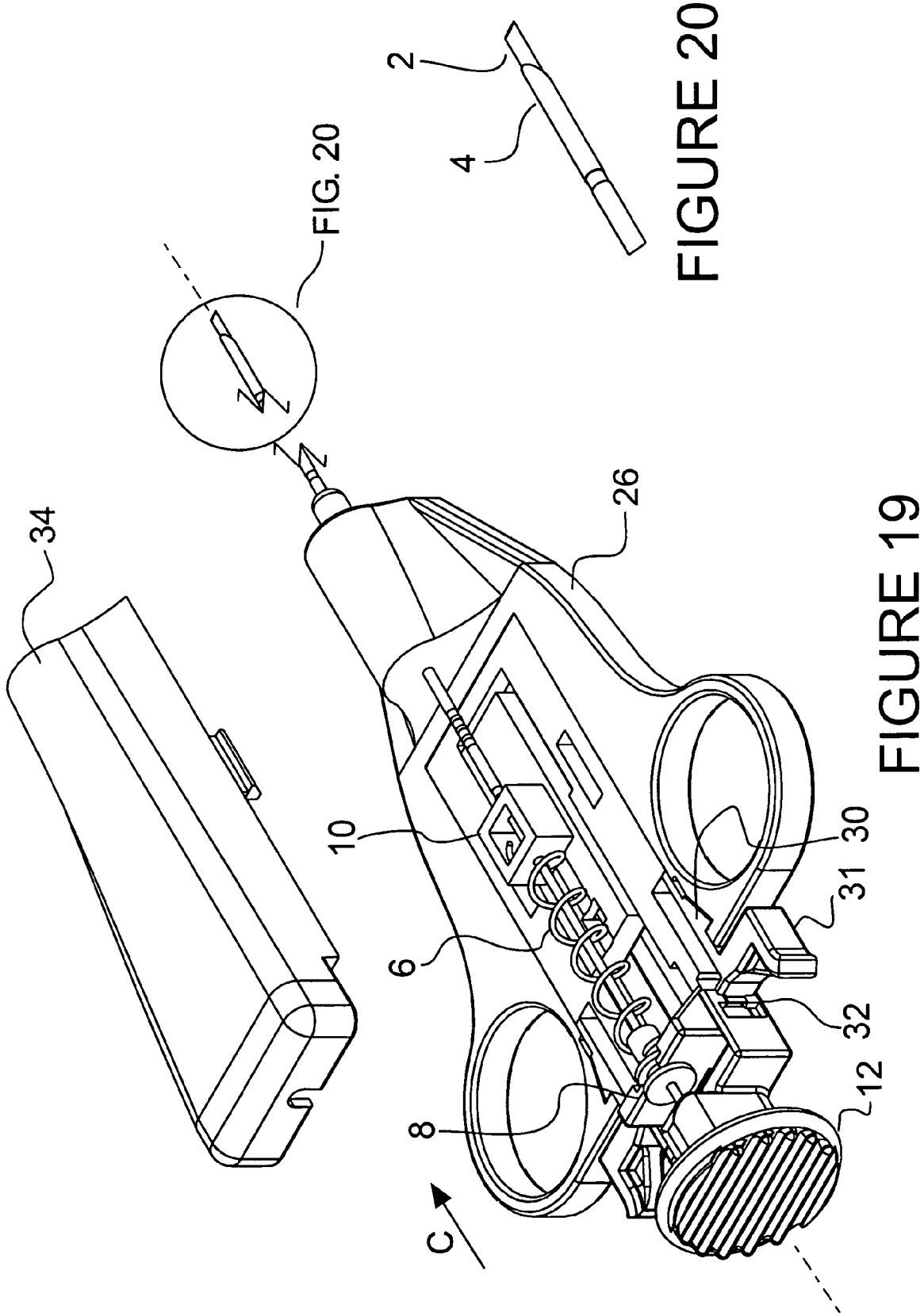

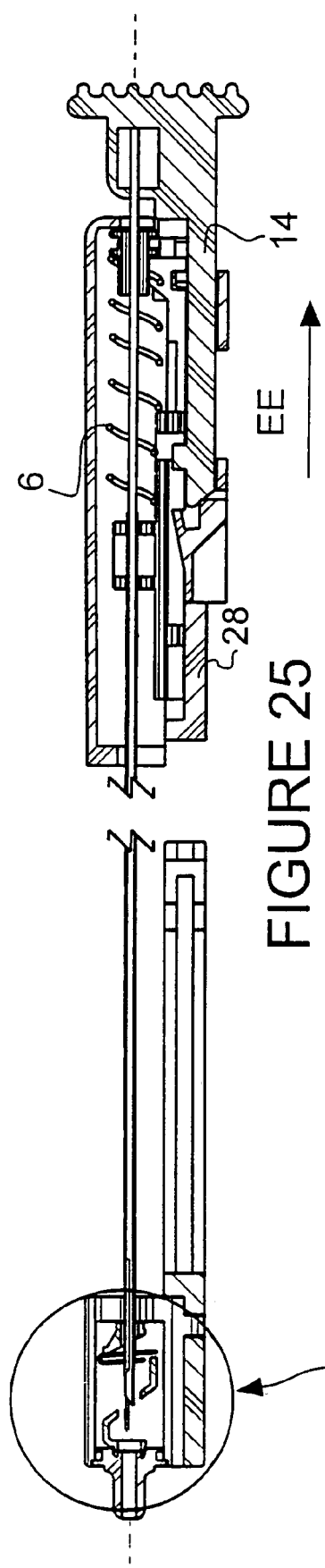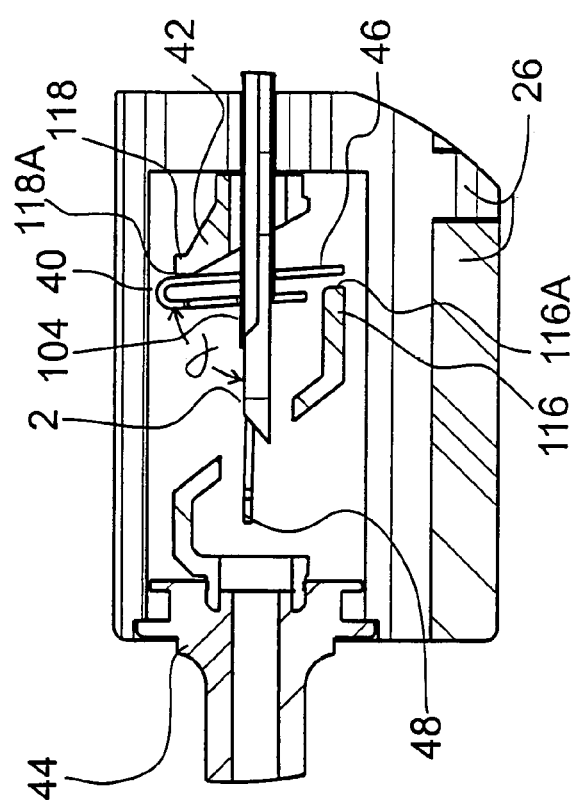
FIGURE 25
FIGURE 26

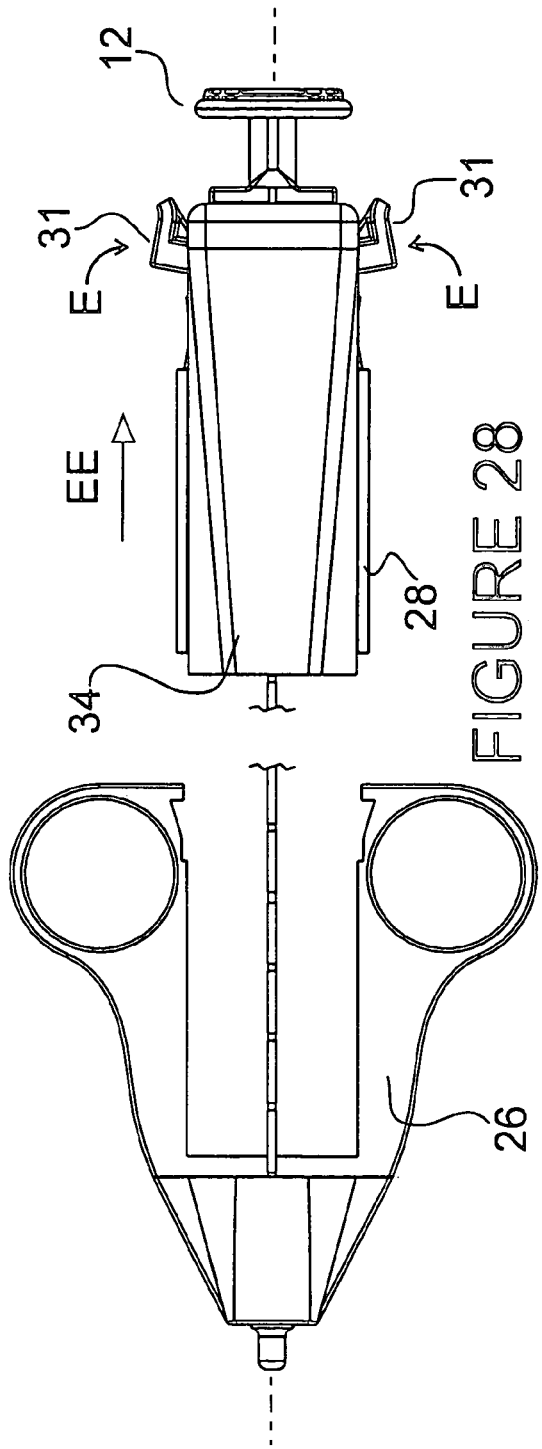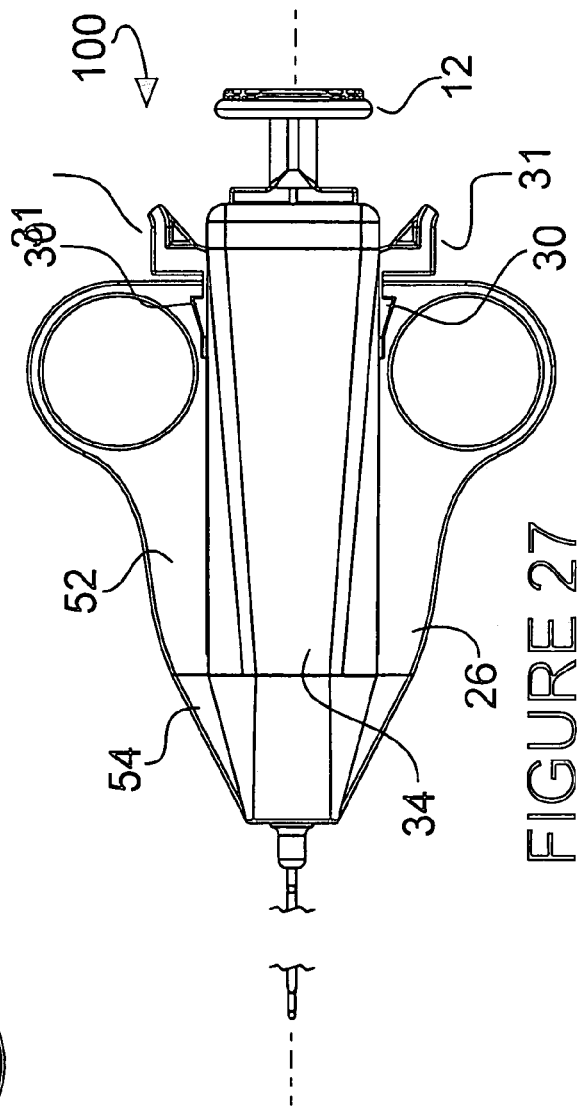

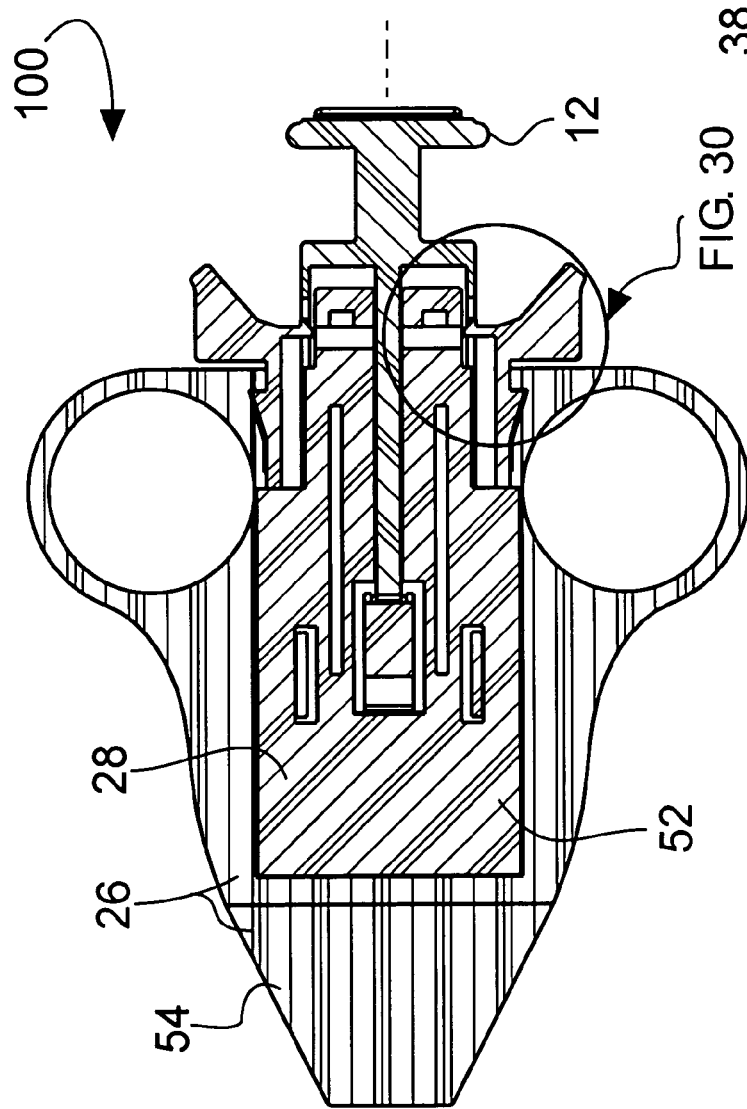
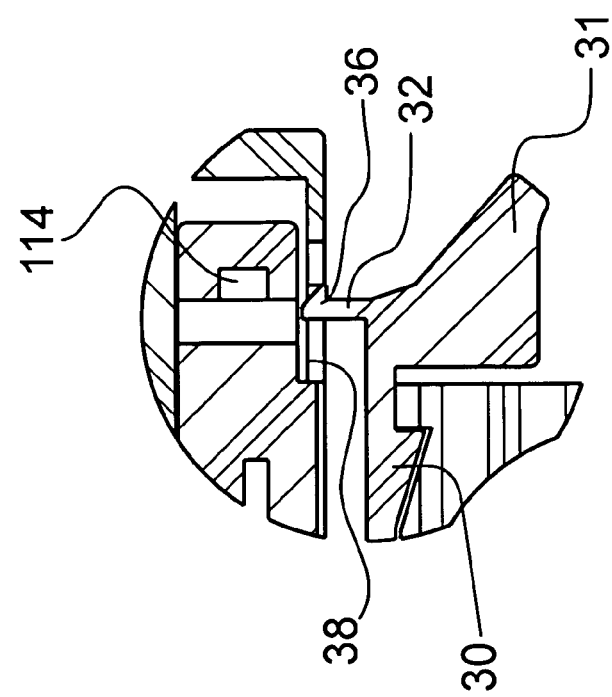
FIGURE 29
FIGURE 30

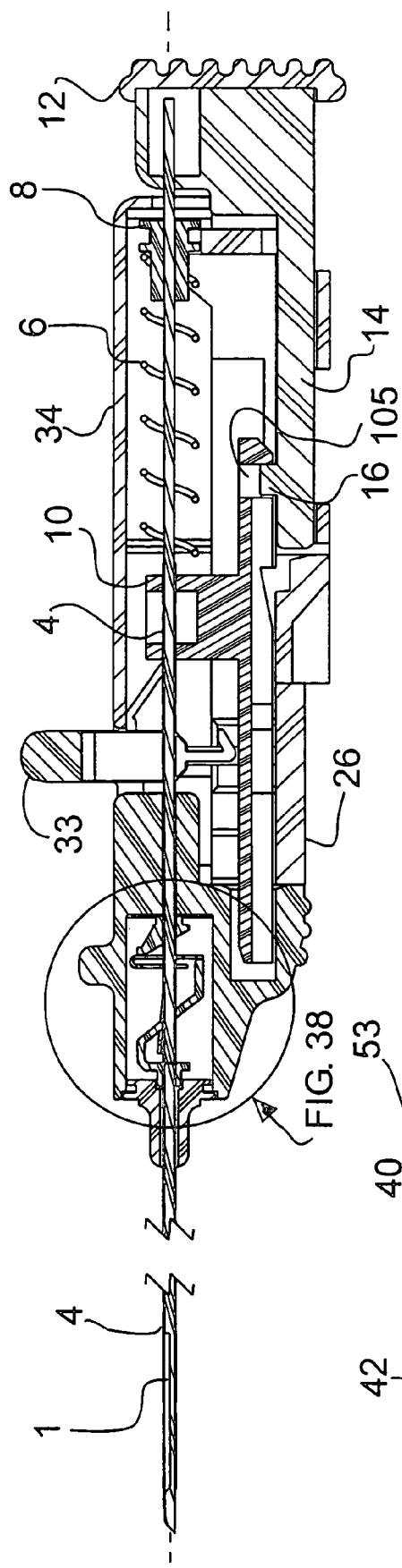
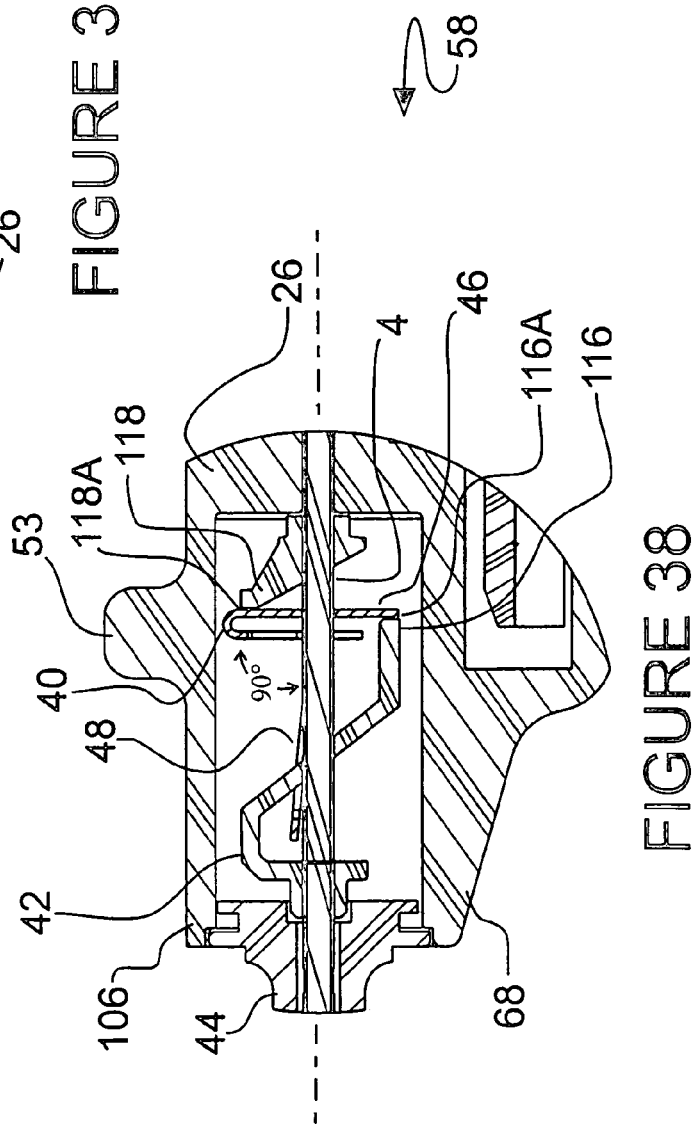
FIGURE 37
FIGURE 38

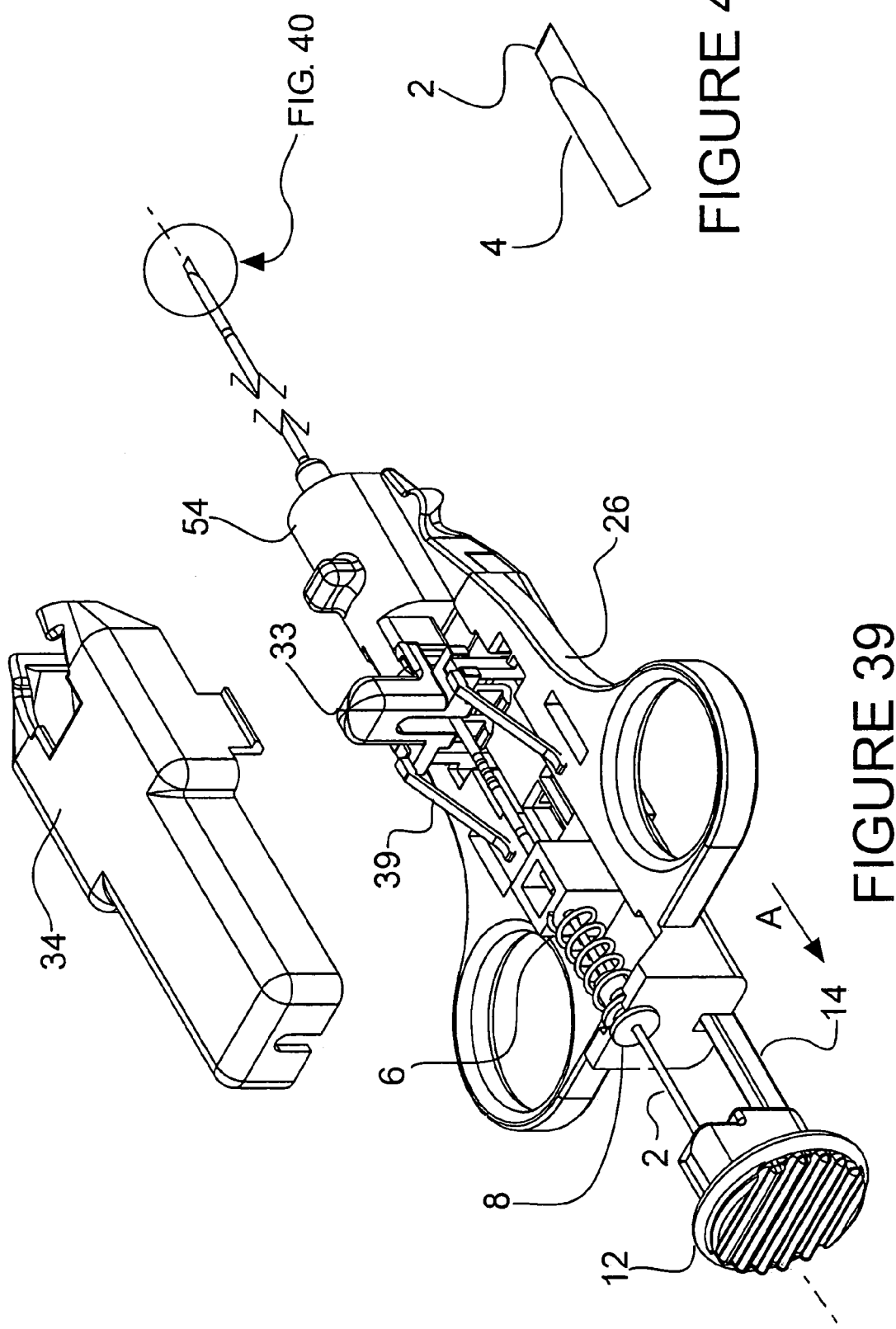

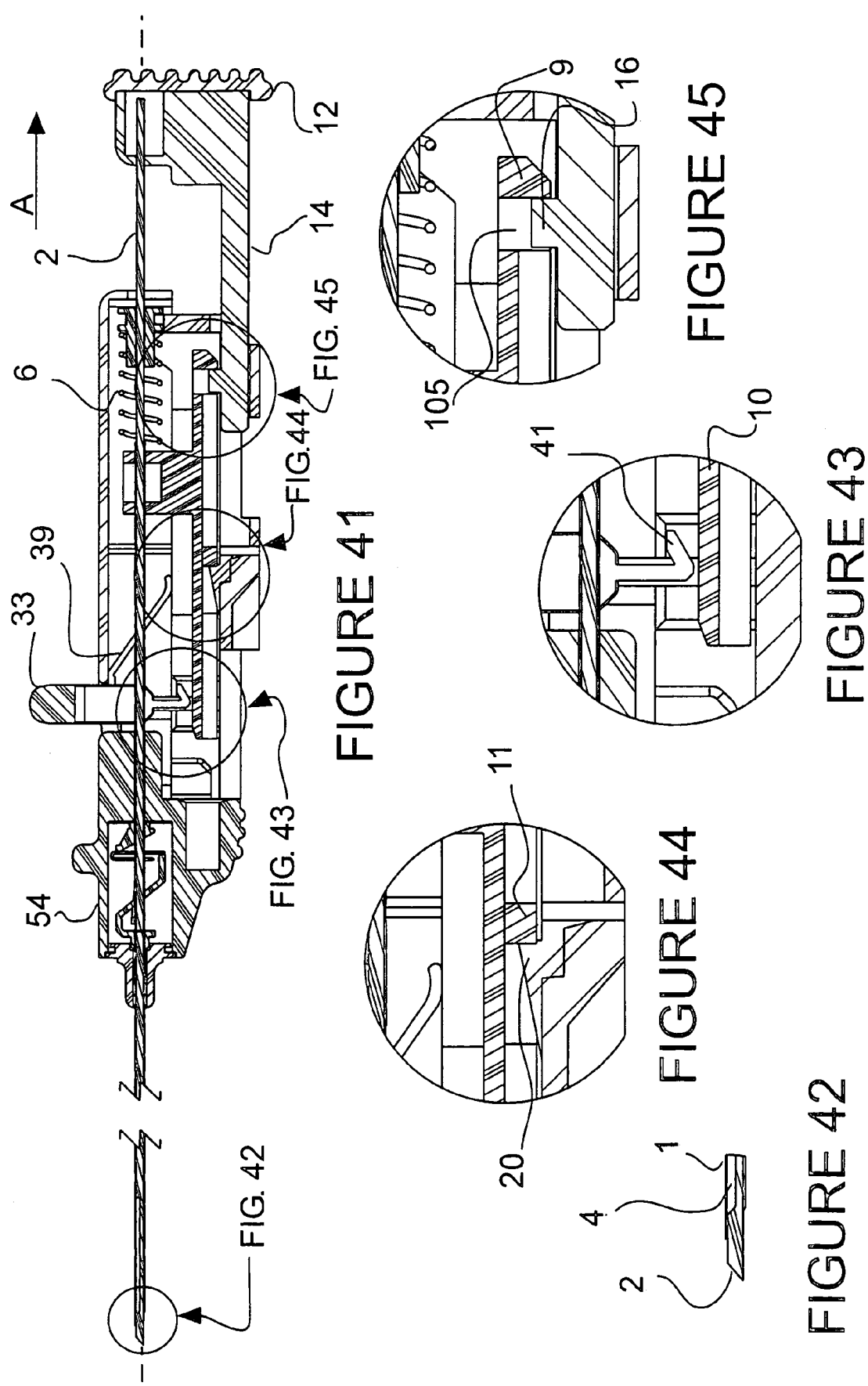

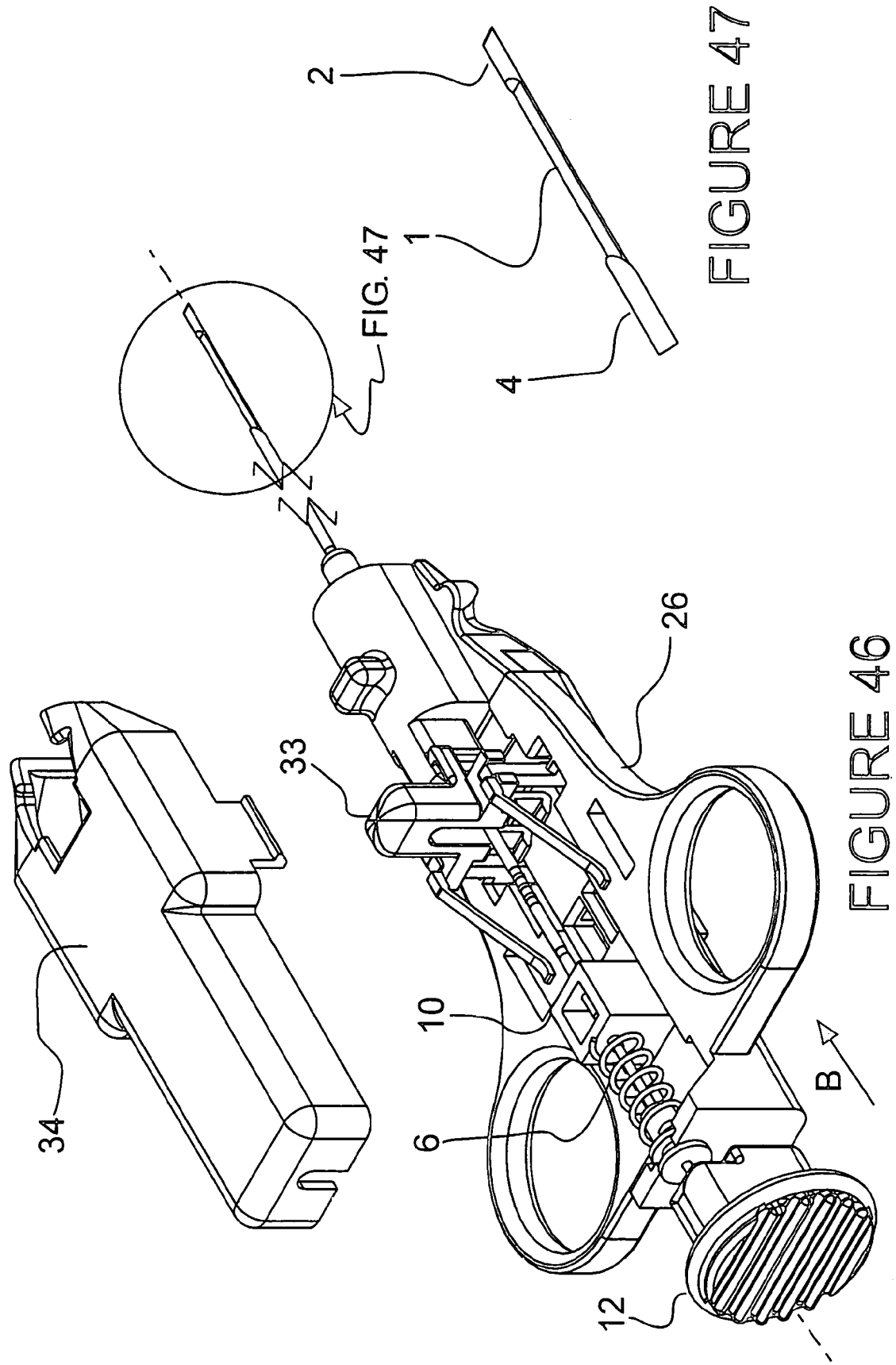

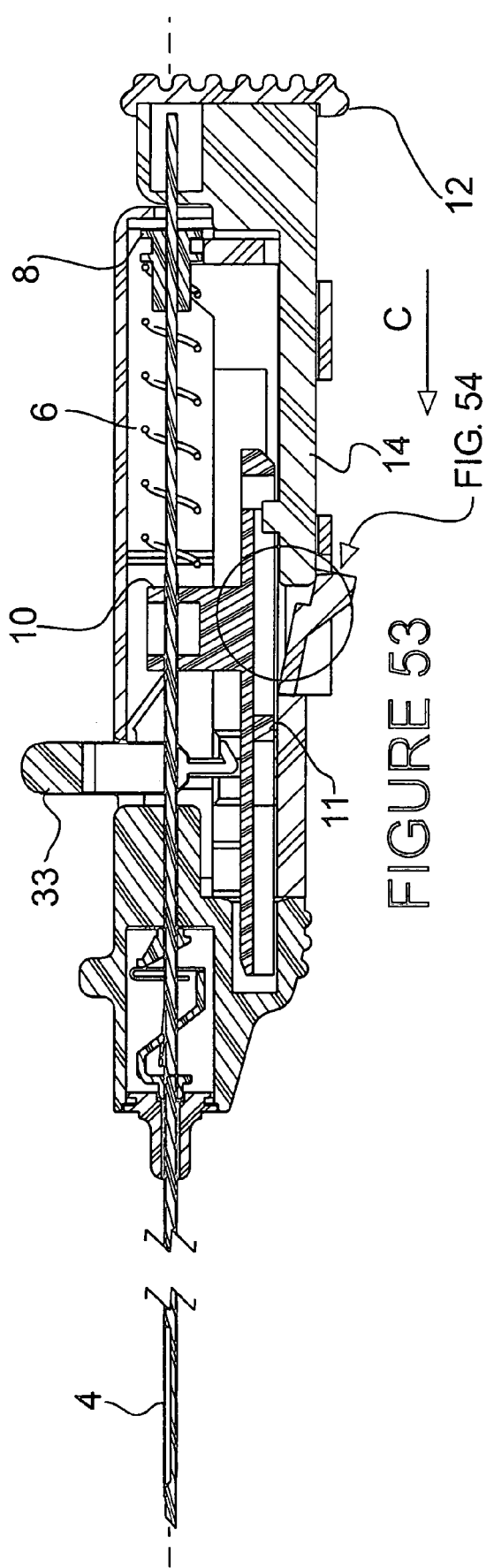
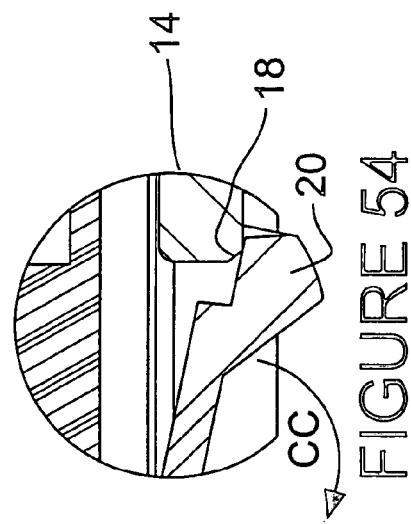
FIGURE 53
FIGURE 54

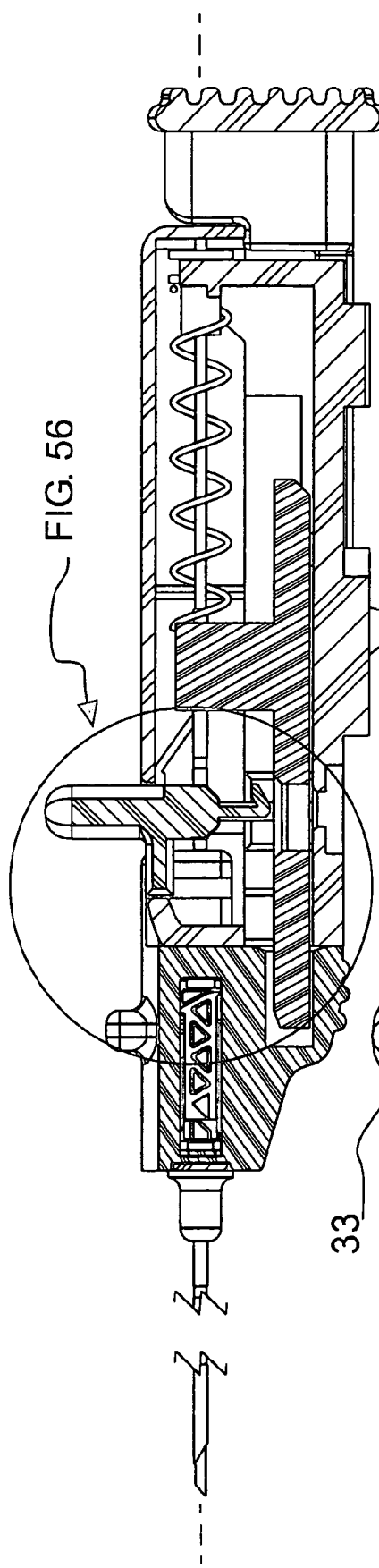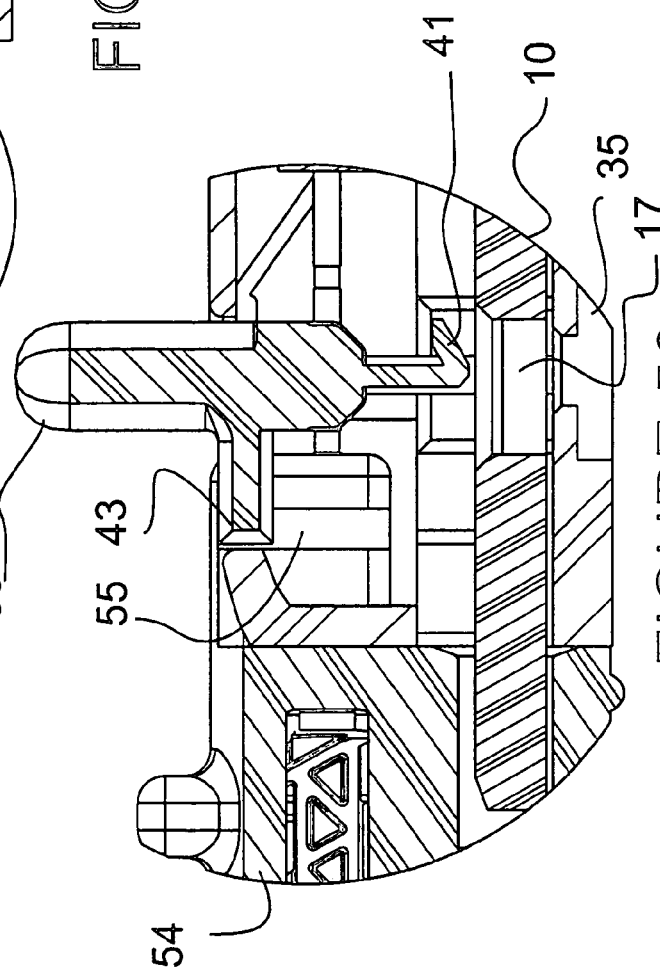
FIGURE 55
FIGURE 56

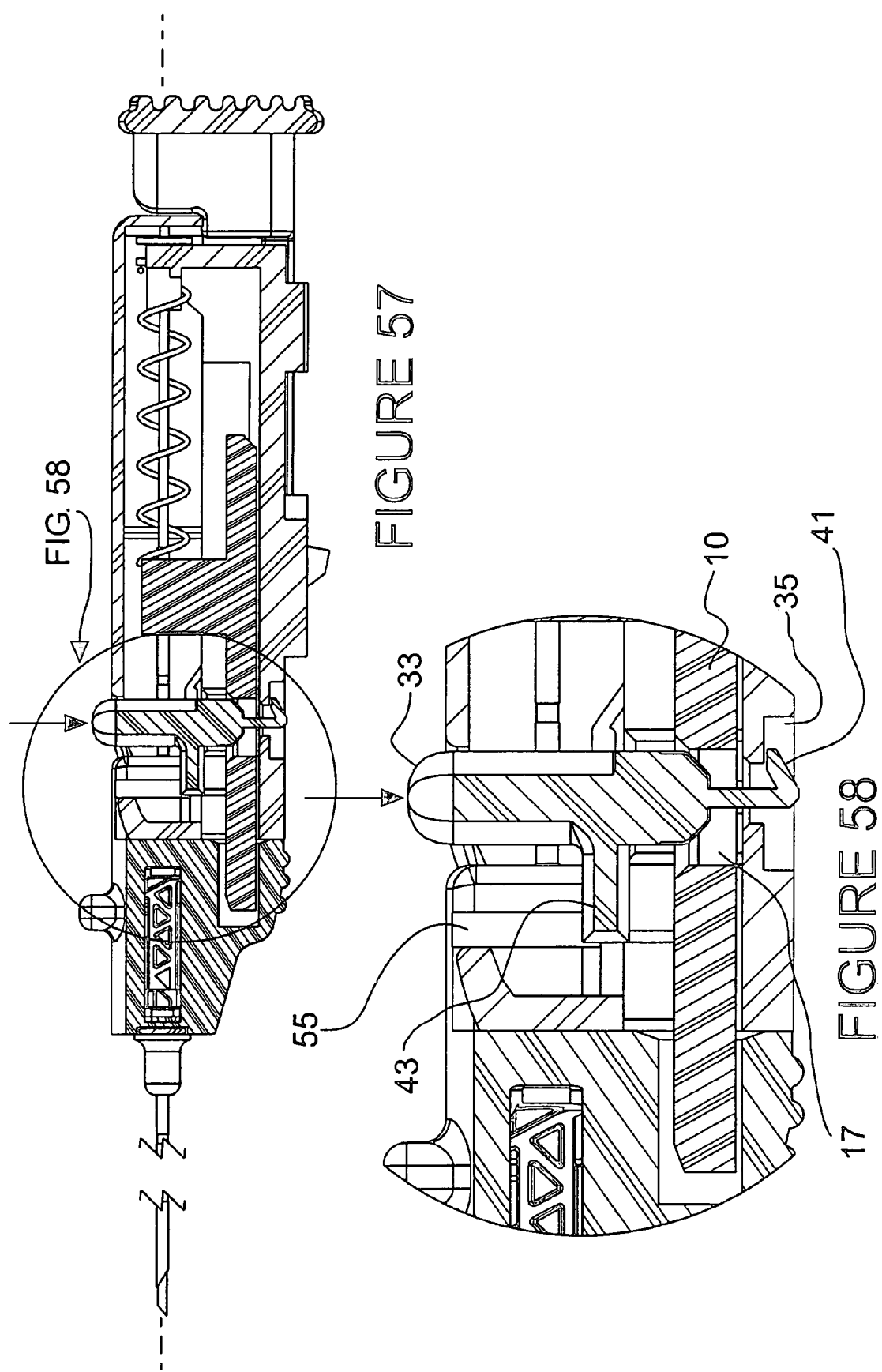

US 6,984,213 B2

BIOPSY NEEDLE DEVICE

CROSS-REFERENCE TO RELATED APPLICATIONS

This patent application is a continuation-in-part of U.S. patent application Ser. No. 10/739,868, filed in the U.S. Patent and Trademark Office on Dec. 18, 2003 by Snow et al., which is a continuation-in-part of U.S. patent application Ser. No. 10/409,819, filed in the U.S. Patent and Trademark Office on Apr. 8, 2003 by Ferguson et al., now U.S. Pat. No. 6,796,962 which is a continuation-in-part of U.S. application Ser. No. 10/322,288, filed in the U.S. Patent and Trademark Office on Dec. 17, 2002 by Ferguson et al., which claims priority to U.S. Provisional Patent application Ser. No. 60/424,655, filed in the U.S. Patent and Trademark Office on Nov. 7, 2002 by Bagley et al., and a continuation-in-part U.S. patent application Ser. No. 10/202,201, filed in the U.S. Patent and Trademark Office on Jul. 23, 2002 by Ferguson et al., now U.S. Pat. No. 6,902,546 which is a continuation-in-part of U.S. patent application Ser. No. 09/809,357, filed in the U.S. Patent and Trademark Office on Mar. 15, 2001 by Ferguson et al., now U.S. Pat. No. 6,595,955 the entire contents of each of these disclosures being hereby incorporated by reference herein.

BACKGROUND

1. Technical Field

The present disclosure generally relates to safety shields for medical needles, and more particularly, to safety shields that protect a needle point of a medical needle for tissue biopsy.

2. Description of the Related Art

Problems associated with inadvertent needle sticks are well known in the art of blood sampling, percutaneous medication injection and other medical procedures involving use of medical needles. Significant attention has been focused on needle stick problems due to the contemporary sensitivity of exposure to AIDS, Hepatitis and other serious blood-borne pathogen exposures.

Procedures for removing a needle from a patient commonly require a technician to use one hand to place pressure at the wound site where the needle is being withdrawn, while removing the needle device with the other hand. It is also common practice for an attending clinician to give higher priority to care for the patient than is given to disposal of a needle. In the case of typical needle devices without safety shields, such priority either requires the convenience of an available sharps container within reach or another means for safe disposal without leaving the patient's side. Providing adequate care while following safety procedures is often compounded by the patient's physical condition and mental state, such as in burn units and psychiatric wards. Under such conditions, it is difficult to properly dispose of a used needle while caring for a patient.

The widespread knowledge and history associated with needle care and disposal problems have resulted in numerous devices for preventing accidental needle sticks. Problems of current safety devices include difficulty of use and high cost due to their complexity and number of parts.

Other known devices employ sheaths that are telescoping, pivoting, etc. These devices, however, may be disadvantageously cumbersome to activate. Further drawbacks of current devices include high manufacturing cost due to complexity and the number of parts. Thus, these type prior art devices may not adequately and reliably shield medical needle apparatus to prevent hazardous exposure.

Consequently, there remains a need to provide a more satisfactory solution for needle safety devices by overcoming the disadvantages and drawbacks of the prior art. Therefore, it would be desirable to provide a more adequate and reliable medical needle shield apparatus that employs a safety shield slidably movable along a medical needle to prevent hazardous exposure to a needle tip. Such a needle shield apparatus should be easily and reliably movable to shield a needle tip of a needle cannula.

SUMMARY

Accordingly, the present disclosure addresses a need for a medical needle shield apparatus for a medical needle for tissue biopsy that effectively and inexpensively protects a tip of a medical needle for tissue biopsy after use. The present disclosure resolves related disadvantages and drawbacks experienced in the art. More specifically, the apparatus and method of this invention constitute an important advance in the art of safety needle devices.

In one particular embodiment, a medical needle shield apparatus is provided in accordance with the principles of the present disclosure. The medical needle shield apparatus includes a first housing that is configured to actuate a needle cannula disposed therewith. A second housing is releasably engageable with the first housing. The needle cannula is disposed for slidable movement with the second housing such that the second housing is extensible from a retracted position to an extended position to enclose a distal end of the needle cannula. The second housing includes a binding member that defines binding surfaces that form an aperture configured for slidable receipt of the needle cannula between the retracted position and the extended position. The binding member includes at least one drag inducing member such that the at least one drag inducing member engages the needle cannula during slidable receipt of the needle cannula to create a drag force with the needle cannula. The drag force facilitates rotation of the binding member relative to a longitudinal axis of the needle cannula such that the binding surfaces engage the needle cannula to prevent slidable movement of the needle cannula in the extended position of the second housing.

The binding member may include a needle communicating surface extending therefrom such that the needle communicating surface is engageable with the needle cannula to prevent rotation of the binding member. The binding member may include a substantially planar aperture plate that includes the binding surfaces that form the aperture. The at least one drag inducing member can include a pair of arms extending from the aperture plate.

The first housing may include a locking configuration that mates with a groove of the second housing to facilitate releasable engagement of the first housing and the second housing. The first housing can include an actuating mechanism that actuates the needle cannula.

The actuating mechanism may include a slide mounted with the needle cannula. The slide facilitates axial movement of the needle cannula. The actuating mechanism can include a biasing member that engages the slide to bias the needle cannula in a distal direction. The actuating mechanism may include a trigger that is connected to the biasing member for actuation thereof.

The second housing may include an inner housing that is disposed with the binding member. The inner housing may define at least one blocking member extending from an interior surface thereof. The at least one blocking member is engageable with the binding member for urging the binding member to a binding orientation.

The needle cannula may include an inner needle disposed for slidable movement with the needle cannula. The inner needle can include a lateral recess disposed adjacent a distal end thereof. Various methods of use of the medical needle shield apparatus are contemplated in accordance with the principles of the present disclosure.

BRIEF DESCRIPTION OF THE DRAWINGS

The foregoing and other features and advantages of the present invention will be more fully understood from the following detailed description of the exemplary embodiments, taken in conjunction with the accompanying drawings in which:

FIG. 5 is a cutaway cross-sectional view of the medical needle shield apparatus shown in FIG. 1;

FIG. 6 is a cross-sectional view of the indicated area of detail shown in FIG. 5;

FIG. 8 is a cutaway perspective view of the medical needle shield apparatus shown in FIG. 1 with a housing section removed;

FIG. 9 is a perspective view of the indicated area of detail shown in FIG. 8;

FIG. 10 is a cutaway cross-sectional view of the medical needle shield apparatus shown in FIG. 1;

FIG. 11 is a cross-sectional view of the indicated area of detail shown in FIG. 10;

FIG. 12 is a cross-sectional view of the indicated area of detail shown in FIG. 10;

FIG. 13 is a cross-sectional view of the indicated area of detail shown in FIG. 10;

FIG. 14 is a cutaway perspective view of the medical needle shield apparatus shown in FIG. 1 with a housing section removed;

FIG. 15 is a perspective view of the indicated area of detail shown in FIG. 14;

FIG. 16 is a cutaway cross-sectional view of the medical needle shield apparatus shown in FIG. 1;

FIG. 17 is a cross-sectional view of the indicated area of detail shown in FIG. 16;

FIG. 18 is a cross-sectional view of the indicated area of detail shown in FIG. 16;

FIG. 19 is a cutaway perspective view of the medical needle shield apparatus shown in FIG. 1 with a housing section removed;

FIG. 20 is a perspective view of the indicated area of detail shown in FIG. 19;

FIG. 25 is a cutaway cross-sectional view of the medical needle shield apparatus shown in FIG. 1 with parts separated;

FIG. 26 is a cross-sectional view of the indicated area of detail shown in FIG. 25;

FIG. 27 is a cutaway top view of the medical needle shield apparatus shown in FIG. 1;

FIG. 28 is a cutaway top view of the medical needle shield apparatus shown in FIG. 1 with parts separated;

FIG. 29 is a cutaway cross-sectional top view of the medical needle shield apparatus shown in FIG. 1;

FIG. 30 is a cross-sectional view of the indicated area of detail shown in FIG. 29;

FIG. 37 is a cutaway cross-sectional view of the medical needle shield apparatus shown in FIG. 34;

FIG. 38 is a cross-sectional view of the indicated area of detail shown in FIG. 37;

FIG. 39 is a cutaway perspective view of the medical needle shield apparatus shown in FIG. 34 with a housing section removed;

FIG. 40 is a perspective view of the indicated area of detail shown in FIG. 39;

FIG. 41 is a cutaway cross-sectional view of the medical needle shield apparatus shown in FIG. 34;

FIG. 42 is a cross-sectional view of the indicated area of detail shown in FIG. 41;

FIG. 43 is a cross-sectional view of the indicated area of detail shown in FIG. 41;

FIG. 44 is a cross-sectional view of the indicated area of detail shown in FIG. 41;

FIG. 45 is a cross-sectional view of the indicated area of detail shown in FIG. 41;

FIG. 46 is a cutaway perspective view of the medical needle shield apparatus shown in FIG. 34 with a housing section removed;

FIG. 47 is a perspective view of the indicated area of detail shown in FIG. 34;

FIG. 53 is a cutaway cross-sectional view of the medical needle shield apparatus shown in FIG. 34;

FIG. 54 is a cross-sectional view of the indicated area of detail shown in FIG. 53;

FIG. 55 is a cutaway cross-sectional view of the medical needle shield apparatus shown in FIG. 34;

FIG. 56 is a cross-sectional view of the indicated area of detail shown in FIG. 55;

FIG. 57 is a cutaway cross-sectional view of the medical needle shield apparatus shown in FIG. 34;

FIG. 58 is a cross-sectional view of the indicated area of detail shown in FIG. 57;

DETAILED DESCRIPTION OF THE EXEMPLARY EMBODIMENTS

Figure 1:
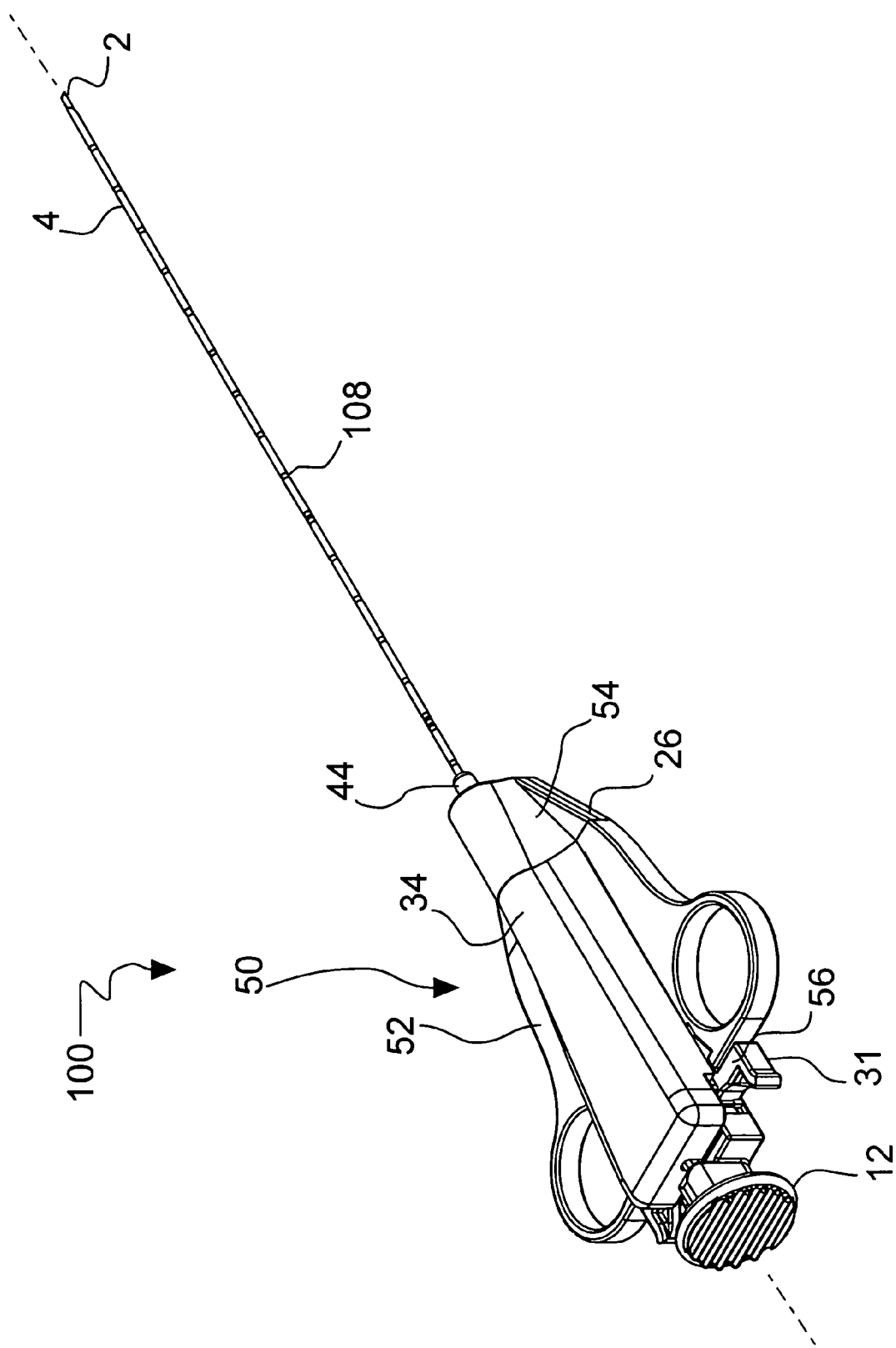
FIG. 1 is a perspective view of one particular embodiment of a medical needle shield apparatus in accordance with the principles of the present disclosure.
Figure 2:
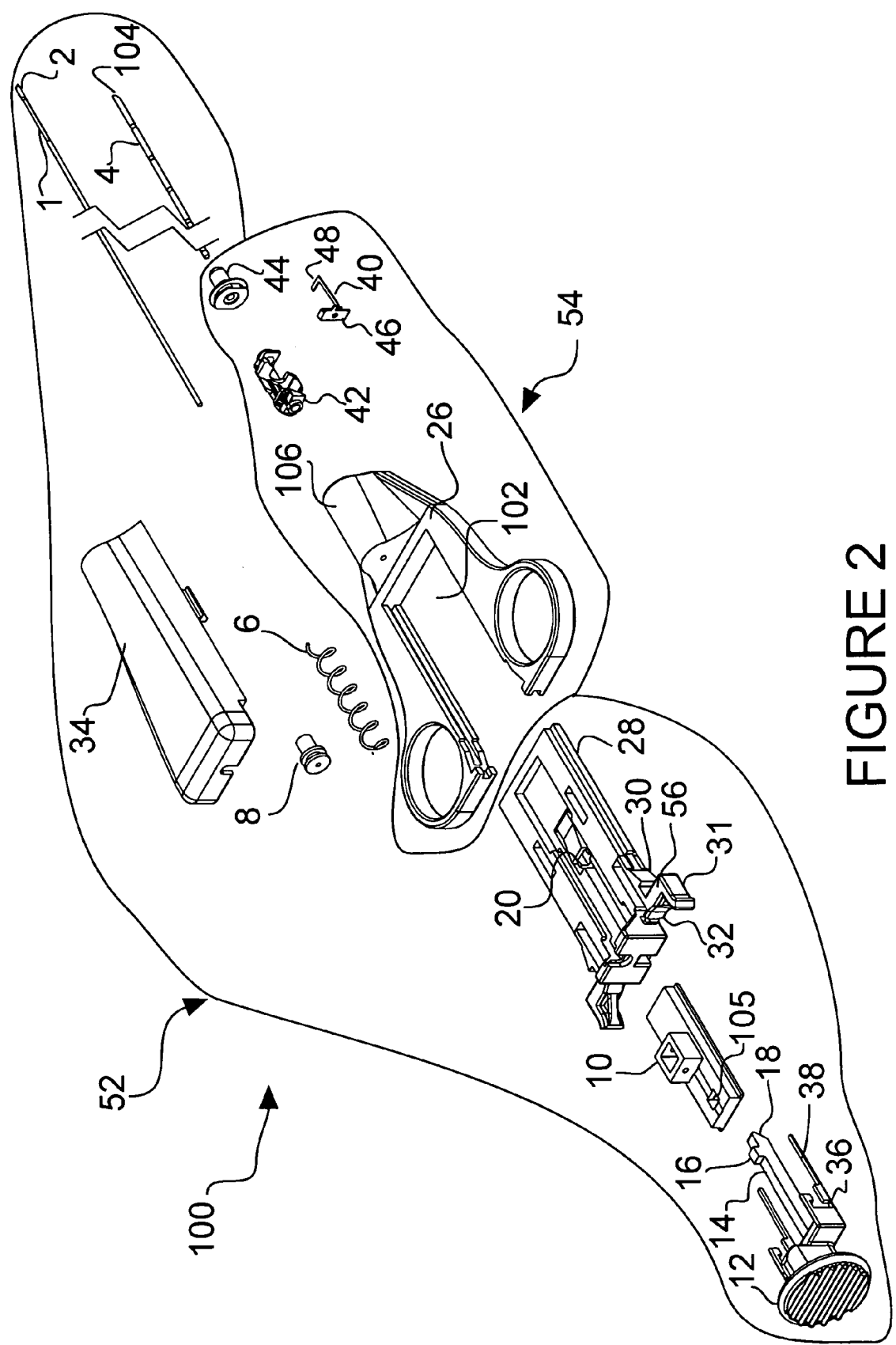
FIG. 2 is a perspective view of the medical needle shield apparatus shown in FIG. 1 with parts separated.

The exemplary embodiments of the medical needle shield apparatus and methods of operation disclosed are discussed in terms of medical needles for tissue biopsy, and more particularly, in terms of needle shield apparatus employed with a needle cannula that prevent hazardous exposure to a needle tip, including, for example, inadvertent needle sticks. It is envisioned that the present disclosure, however, finds application to a wide variety of cannula needles, stylettes and devices for tissue biopsy, sampling, etc. Such devices may include mechanisms for actuating a needle cannula, such as, for example, semi-automatic soft tissue biopsy needles, semi-automatic soft tissue biopsy guns, automatic soft tissue biopsy devices, etc.

In the discussion that follows, the term "proximal" refers to a portion of a structure that is closer to a clinician, and the term "distal" refers to a portion that is further from the clinician. As used herein, the term "subject" refers to a patient having tissue biopsy using the medical needle shield apparatus. According to the present disclosure, the term "clinician" refers to an individual performing tissue collection, installing or removing a needle cannula from a medical needle shield apparatus and may include support personnel.

The following discussion includes a description of the medical needle shield apparatus, followed by a description of the method of operating the medical needle shield apparatus in accordance with the present disclosure. Reference will now be made in detail to the exemplary embodiments of the disclosure, which are illustrated in the accompanying figures.

Turning now to the figures, wherein like components are designated by like reference numerals throughout the several views. Referring initially to FIGS. 1–7, there is illustrated a medical needle shield apparatus 100, constructed in accordance with the principals of the present disclosure. Medical needle shield apparatus 100 has a body 50 that includes a first housing, such as, for example, body core 52. Body core 52 includes an actuating mechanism that actuates a needle cannula 4 disposed therewith. The actuating mechanism, an example of which is described below, advances needle cannula 4 to facilitate tissue sampling, as will be discussed.

Needle cannula 4 includes a cutting edge, echogenic features and depth markings 108. An inner needle, such as, for example, stylette 2 is disposed for slidable movement within needle cannula 4. Needle cannula 4 is concentric with stylette 2. Stylette 2 has a cutting edge and a recess 1 configured to capture tissue samples, as will be discussed.

Body core 52 encloses components disposed therein with a core cover 34. It is envisioned that core cover 34 may be variously configured and dimensioned such as, for example, rectangular, spherical, etc. It is further envisioned that core cover 34 may be assembled by any appropriate process such as, for example, snap fit, adhesive, solvent weld, thermal weld, ultrasonic weld, screw, rivet, etc. Alternatively, body core 52 may be monolithically formed or integrally assembled of multiple housing sections and may be substantially transparent, opaque, etc. Body core 52 may include ribs, ridges, etc. to facilitate manipulation of medical needle shield apparatus 100.

A second housing, such as, for example, a body base 54 includes a base handle 26. Base handle 26 defines a cavity 102 configured for receipt of body core 52 such that body core 52 is releasably engageable with body base 54. Needle cannula 4 is disposed for slidable movement with body base 54 such that body base 54 is extensible from a retracted position (FIG. 1) to an extended position (FIG. 33) to enclose a sharp distal end 104 of needle cannula 4.

Figure 7:
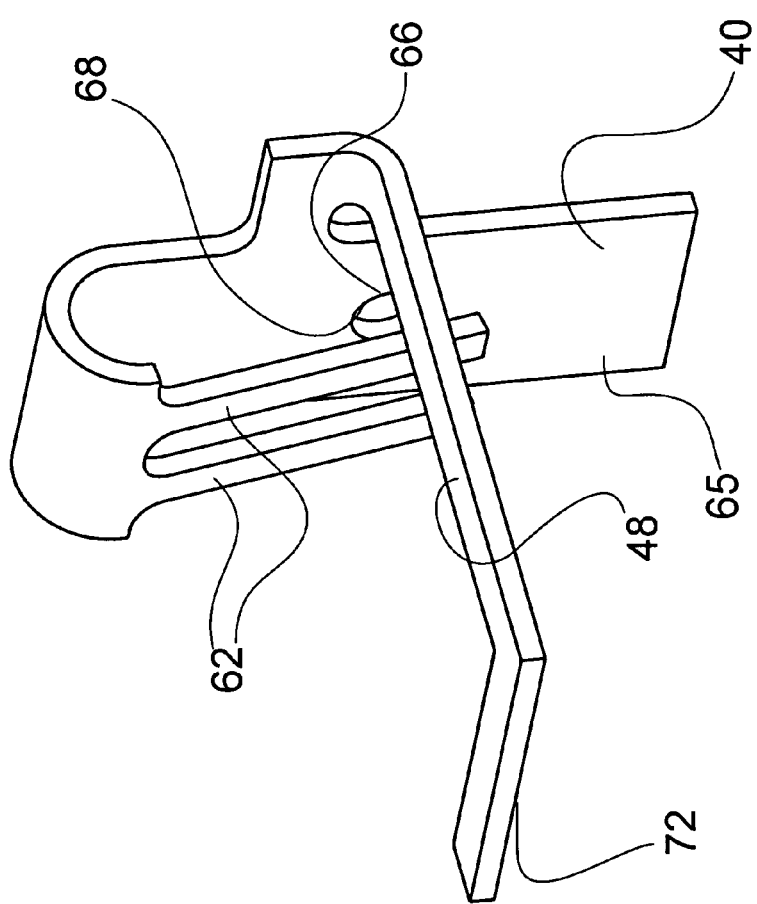
FIG. 7 is an enlarged perspective view of a binding member of the medical needle shield apparatus shown in FIG. 1.

Body base 54 includes a binding member 40 that defines binding surfaces 68 (FIGS. 6–7). Binding surfaces 68 form an aperture 66 configured for slidable receipt of needle cannula 4 between the retracted position and the extended position. Aperture 66 is formed in an aperture plate 65. Binding member 40 may be monolithically formed and aperture plate 65 has a rectangular, generally planar configuration with sufficient stiffness to produce forces for binding needle cannula 4, as will be discussed. It is envisioned that aperture plate 65 may have an arcuate surface, undulating, etc. It is further envisioned that aperture plate 65 may have various degrees of stiffness according to the requirements of a particular application.

Binding member 40 includes at least one drag inducing member, such as, for example, friction members 62. Friction members 62 engage needle cannula 4 during slidable receipt of needle cannula 4 to create a drag force with needle cannula 4 between the retracted position and the extended position. Inner housing 42 includes blocking members 116, 118 configured to engage binding member 40 and are disposed not to interfere with needle cannula 4. Blocking members 116, 118 define surfaces 116A, 118A respectively, that facilitate disposal of aperture plate 65 from a non-binding or sliding orientation (FIG. 6) to a binding orientation (FIG. 26). Blocking members 116 and/or 118 cause binding member 40 to move to the binding orientation, in conjunction with the frictional drag force created between friction members 62 and needle cannula 4, as body base 54 is manipulated in the distal direction along longitudinal axis x. The force created by blocking members 116 and/or 118 acts in a direction opposite to the drag force, causing a force couple, which rotates binding member 40 to the binding orientation.

The frictional drag force in conjunction with blocking members 116 and/or 118 generates a canting force and inclination of aperture plate 65, relative to longitudinal axis x. The canting force urges rotation of binding member 40 and causes a lever or moment of end sensing member 48, which is opposed by needle cannula 4 to prevent rotation of binding member 40 in the sliding orientation.

Frictional members 62 may be monolithically formed with binding member 40 and extend from aperture plate 65 for alignment with aperture 66 and engagement with needle cannula 4. Frictional members 62 are spaced apart to facilitate sliding engagement with needle cannula 4. Such engagement creates the frictional drag force with needle cannula 4. It is envisioned that one or a plurality of friction members 62 may be employed. It is contemplated that frictional members 62 may be flexible or have flexible portions, which may be of varying flexibility according to the particular requirements of a needle application.

Binding member 40 also includes an end sensing member 48 extending therefrom. End sensing member 48 has a needle communicating surface 72 that is engageable with needle cannula 4 to prevent rotation of binding member 40. It is envisioned that needle communicating surface 72 may include ribs, projections, cavities, etc. for engagement with needle cannula 4 or that a portion of needle communicating surface 72 engages needle cannula 4.

Body base 54 includes a housing section 106 that encloses binding member 40 and adjacent components. It is envisioned that housing section 106 may be variously configured and dimensioned such as, for example, rectangular, spherical, etc. It is further envisioned that housing section 106 may be assembled by any appropriate process such as, for example, snap fit, adhesive, solvent weld, thermal weld, ultrasonic weld, screw, rivet, etc. Alternatively, body base 54 may be monolithically formed or integrally assembled of multiple housing sections and may be substantially transparent, opaque, etc. Body base 54 may include ribs, ridges, etc. to facilitate manipulation of medical needle shield apparatus 100.

The components of medical needle shield apparatus 100 can be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate.

The actuating mechanism includes a coring cannula slide 10 disposed within body core 52 and slidable relative thereto. Needle cannula 4 is mounted with coring cannula slide 10 for corresponding movement therewith. Coring cannula slide 10 is supported by a base safety slide 28 and enclosed by core cover 34. It is envisioned that coring cannula slide 10 may be variously configured and dimensioned such as, for example, rectangular, spherical, etc.

Base safety slide 28 is slidably received by cavity 102 for assembly of body core 52 and body base 54. Stylette 2 is mounted with a trigger-setting button 12 to facilitate actuation thereof and supported for movement relative to body core 52 via a bushing 8. Bushing 8 facilitates alignment and relative slidable movement of stylette 2 with body core 52 during use. It is envisioned that stylette 2 may be supported for movement with body core 52 without bushing 8.

Trigger-setting button 12 is operably connected to coring cannula slide 10 to facilitate actuation of needle cannula 4. Trigger-setting button 12 connects to coring cannula slide 10 via a biasing member, such as, for example, spring 6 and safety slide 28. Spring 6 is disposed within body core 52, concentrically about stylette 2. Spring 6 is mounted onto bushing 8 and into engagement with a proximal portion of coring cannula slide 10 for driving slide 10 during expansion. Trigger-setting button 12 is operative with a trigger-setting arm 14, which is configured to facilitate actuation of needle cannula 4 and stylette 2, as will be discussed.

Figures 3, 4:
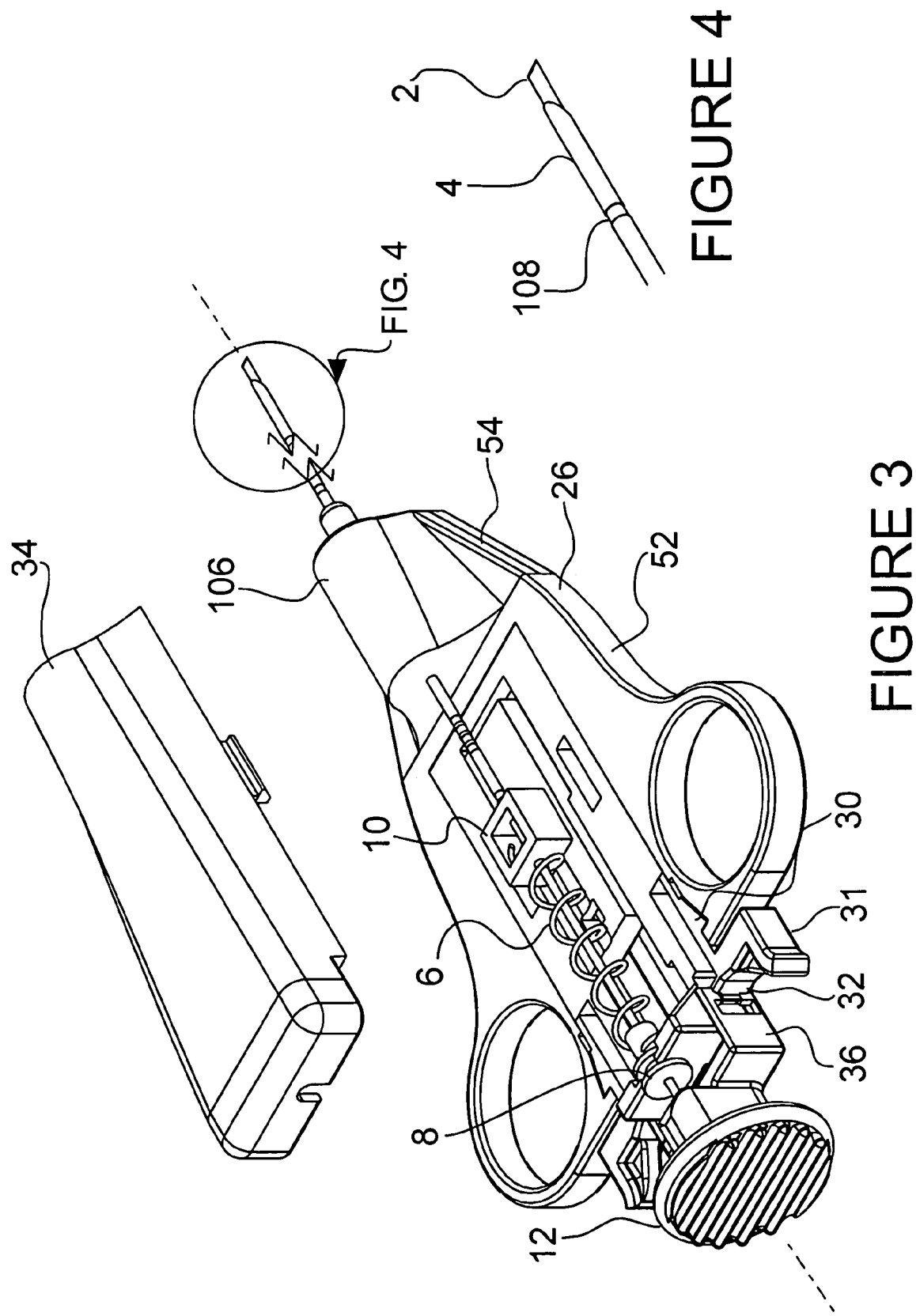
FIG. 3 is a cutaway perspective view of the medical needle shield apparatus shown in FIG. 1 with a housing section removed.
FIG. 4 is a perspective view of the indicated area of detail shown in FIG. 3.

In a primary state of medical needle shield apparatus 100, as shown in FIGS. 1, 3 and 5, spring 6 is expanded and trigger-setting button 12 and coring cannula slide 10 are in a distal position on safety slide 28. Needle cannula 4 and stylette 2 are attached to coring cannula slide 10 and trigger-setting button 12, respectively, each in a distal position. In such a distal position, recess 1 of stylette 2 is enclosed by needle cannula 4, as shown in FIG. 4. Binding member 40 is in a non-binding or sliding orientation, as will be discussed, which allows needle cannula 4 to slide freely.

To set the actuating mechanism, trigger-setting button 12 is manipulated in a proximal direction along longitudinal axis x, in the direction of arrow A shown in FIGS. 8 and 10. Needle cannula 4 maintains enclosure of recess 1 of stylette 2, as shown in FIG. 9. Trigger-setting arm 14 includes a trigger-setting tooth 16, which is configured for disposal within a groove 105 of coring cannula slide 10. Disposal of trigger-setting tooth 16 within groove 105 causes corresponding engagement with proximal slide stop 9, as shown in FIG. 13. Correspondingly, a distal slide stop 11 of coring cannula slide 10 engages a compression lock 20, as shown in FIG. 12. Proximal slide stop 9 and distal slide stop 11 thereby facilitate maintenance of the actuating mechanism in a set position. Proximal movement of trigger-setting button 12 also compresses spring 6 into a set position. In the set position, needle cannula 4 maintains enclosure of recess 1 of stylette 2, as shown in FIG. 11.

In contemplation of actuation of needle cannula 4, trigger-setting button 12 is manipulated in a distal direction, as shown by arrow B in FIGS. 14 and 16, until resistance is encountered. For example, a source of resistance to the distal manipulation can include engagement of a trigger core activating ramp 18 with compression lock 20, as shown in FIG. 18. The distal manipulation of trigger-setting button 12 forces stylette 1 forward and exposes recess 1, as shown in FIGS. 15 and 17, while spring 6 is maintained in compression.

Figure 21:
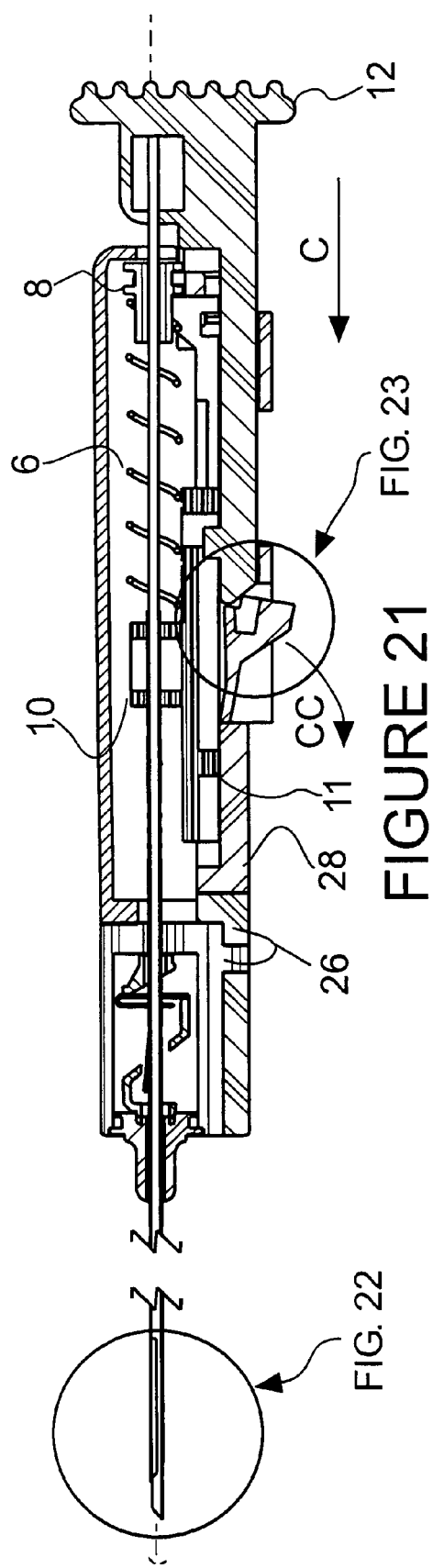
FIG. 21 is a cutaway cross-sectional view of the medical needle shield apparatus shown in FIG. 1.
Figure 23:
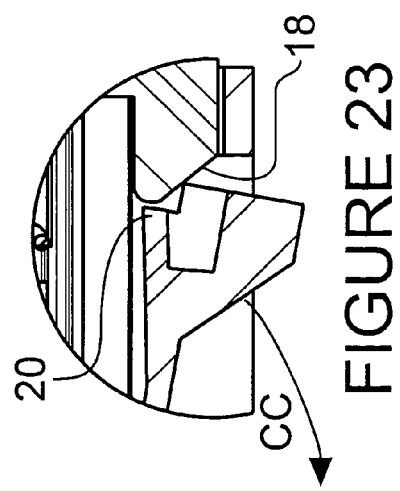
FIG. 23 is a cross-sectional view of the indicated area of detail shown in FIG. 21.
Figure 22:
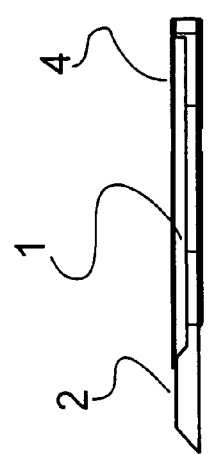
FIG. 22 is a cross-sectional view of the indicated area of detail shown in FIG. 21.
Figure 24:
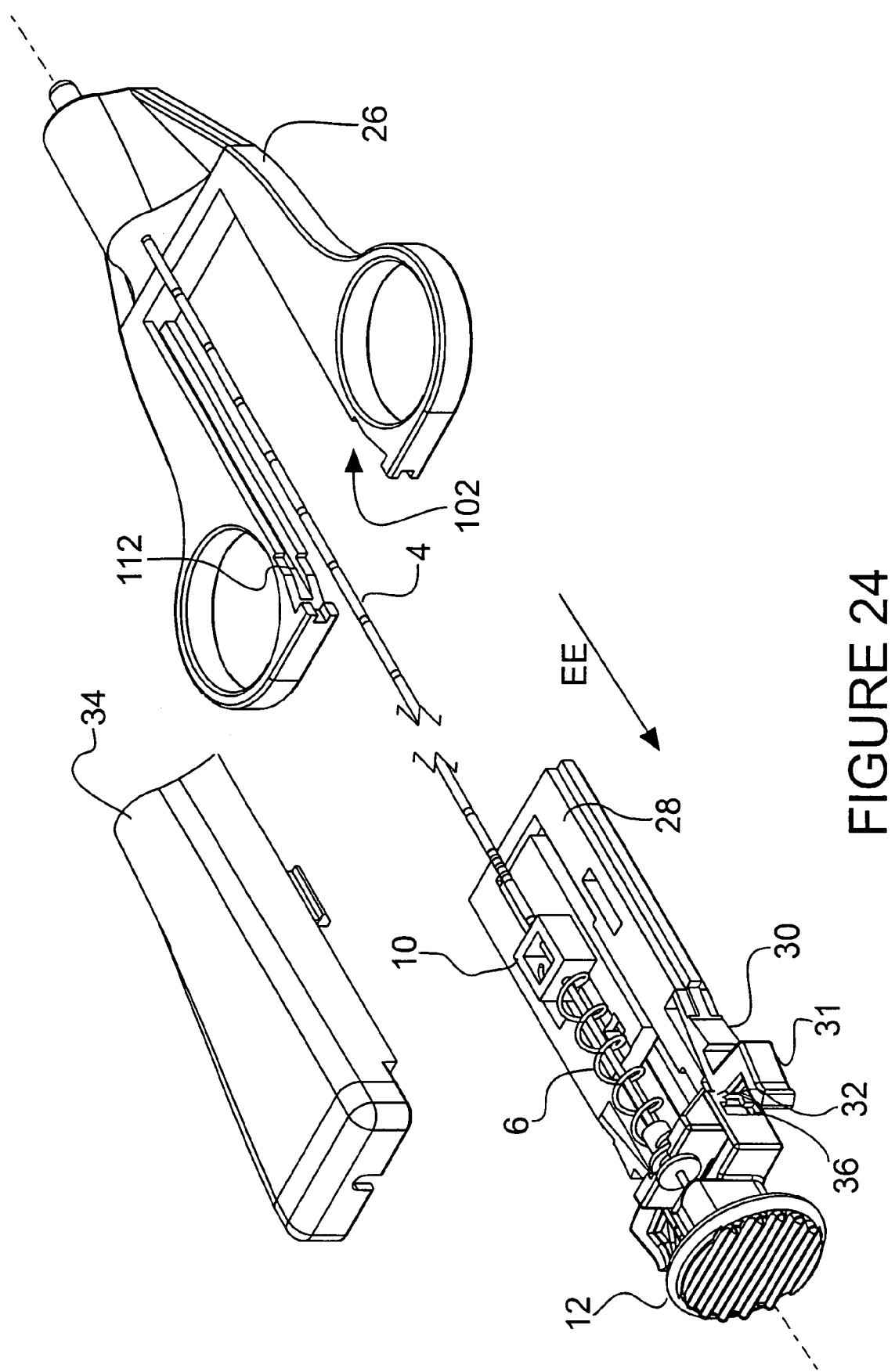
FIG. 24 is a cutaway perspective view of the medical needle shield apparatus shown in FIG. 1 with parts separated.
Figures 31, 32:
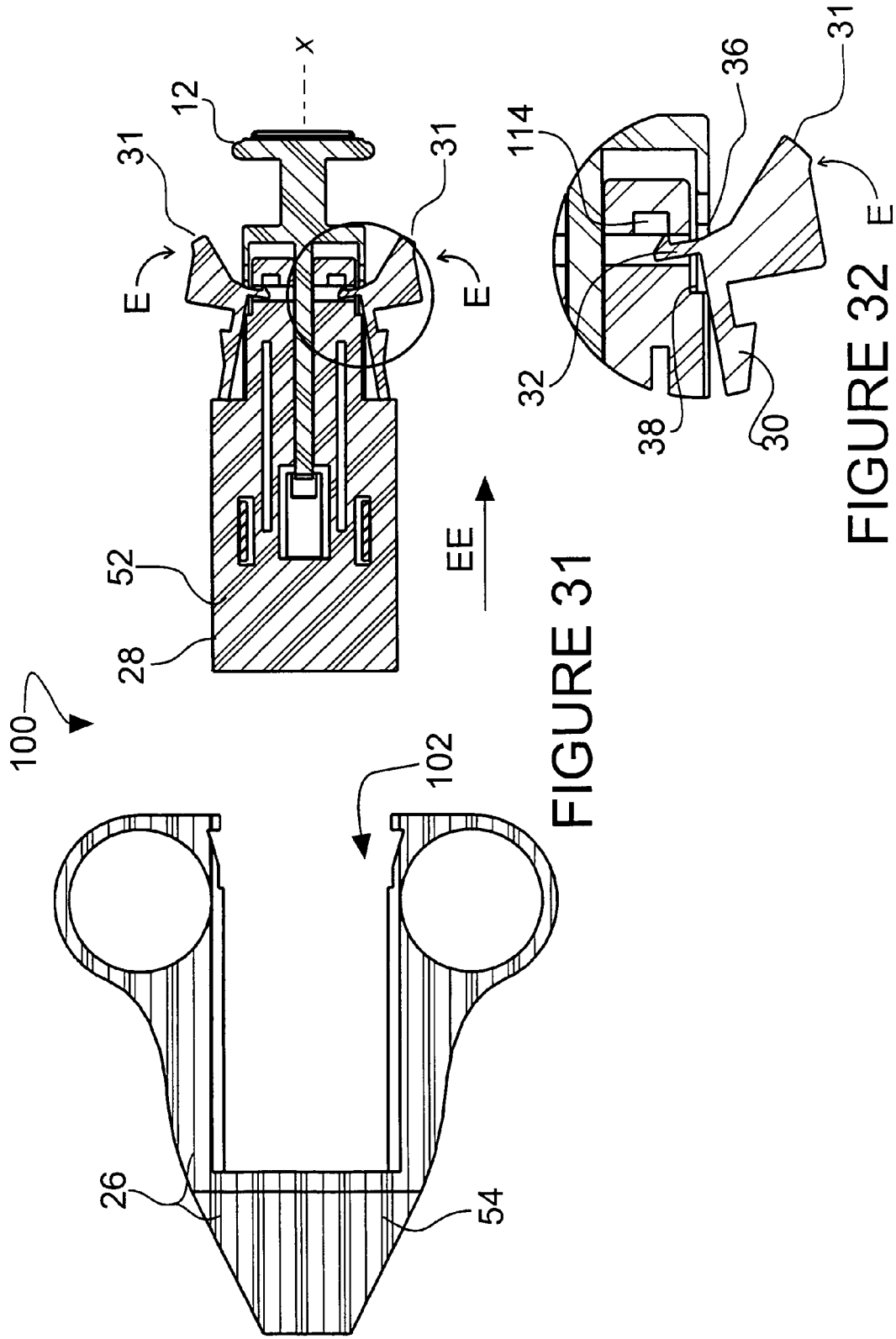
FIG. 31 is a cutaway cross-sectional top view of the medical needle shield apparatus shown in FIG. 1 with parts separated.
FIG. 32 is a cross-sectional view of the indicated area of detail shown in FIG. 31.

In an exemplary actuation, needle cannula 4 and stylette 2 are placed through soft tissue of a subject (not shown) to a desired location, which may be viewed via echogenic and depth markings 108. At the desired location, a tissue sample for biopsy enters recess 1. Trigger-setting button 12 is manipulated distally beyond the initial resistance of trigger core activating ramp 18 with compression lock 20, as shown by arrow C in FIG. 21. Further manipulation of button 12 drives trigger core activating ramp 18 to deflect compression lock 20 such that distal slide stop 11 disengages from compression lock 20, as shown by arrow CC in FIGS. 21 and 23. Thus, coring cannula slide 10 is thrust, via spring 6, to a distal position, as shown by arrow D in FIG. 19. Correspondingly, needle cannula 4 is thrust distally to core and enclose the soft tissue within recess 1, as shown in FIGS. 20 and 22. The captured soft tissue sample is then withdrawn from the subject.

The captured soft tissue sample is removed by resetting the actuating mechanism and distally manipulating button 12 to expose recess 1, as described above, outside of the subject. Additional soft tissue sampling may be repeated with medical needle shield apparatus 100.

Referring to FIGS. 24–28, upon completion of soft tissue sampling, body core 52 and body base 54 may be disassembled via inward manipulation of base assembly locking arms 31, as shown by arrow E in FIG. 28, and pulled proximally, in the direction shown by arrow EE, while base handle 26 is held in a fixed position. A base assembly locking tooth 30, disposed with safety slide 28 disengages from a mating groove 112 of base handle 26. This configuration advantageously separates body core 52 and body base 54.

In an alternate embodiment, as shown in FIGS. 29–32, separating body core 52 and body base 54, in conjunction with manipulating base assembly locking arms 31 occurs only when medical needle shield apparatus 100 is in the primary state, as described. A trigger slide 38 of safety slide 28 provides a physical stop verification when the actuating mechanism is triggered. Trigger slide 38, in the triggered position, is aligned with base assembly locking arms 31 and prevents manipulation of arms 31.

In the primary state, trigger slide 38 is disposed such that base assembly locking arms 31 are aligned with a trigger safety lockout gap 36, as shown in FIG. 30. Base assembly locking arms 31 may be manipulated for inward movement. A base trigger safety lockout tooth 32 of arms 31 is deflected through the trigger safety lockout gap 36 and locks with an inner gap 114 of safety slide 28, as shown by arrow E in FIG. 32. This configuration facilitates separation of body 50 and prevents activation of the actuating mechanism while binding member 40 is in a binding orientation, as will be discussed.

Body base 54 is extensible from a retracted position (FIG. 1) to an extended position (FIG. 33) to enclose distal end 104 of needle cannula 4. Binding member 40 is supported within body base 54 via an inner housing 42 and base handle 26, as shown in FIG. 6. A cap 44 supports inner housing 42 with base handle 26 and facilitates slidable movement of needle cannula 4. Inner housing 42 is substantially cylindrical and may alternatively be variously configured and dimensioned such as, for example, rectangular, spherical, etc. It is contemplated that binding member 40 is rotatable about needle cannula 4 with inner housing 42. It is further contemplated that inner housing 42 is rotatable about needle cannula 4 with body base 54, or alternatively, relative to body base 54.

End sensing member 48 extends distally from aperture plate 65, parallel to needle cannula 4. End sensing member 48 is perpendicularly oriented relative to a plane defined by aperture plate 65. This perpendicular orientation facilitates inclination of aperture plate 40 for disposal in a binding or sliding orientation of binding member 40. It is envisioned that end sensing member 48 may be variously oriented with aperture plate 65 and may flexibly extend therefrom.

As needle cannula 4 is released from engagement with needle communicating surface 72, binding member 40 and end sensing member 48 rotate to the binding orientation. Corresponding rotation of aperture plate 65 causes binding surfaces 68 to frictionally engage needle cannula 4 and prevent movement thereof. Blocking members 116, 118 cause aperture plate 65 to move to the binding orientation as forces are imposed on body base 54 in either direction along longitudinal axis x.

In the binding orientation, proximal manipulation of needle cannula 4 causes aperture plate 65 to engage binding member 118 resulting in further counterclockwise inclination and enhanced frictional engagement of binding surfaces 68 with needle cannula 4. Distal manipulation of needle cannula 4 similarly causes aperture plate 65 to engage binding member 116 resulting in further counterclockwise inclination and enhanced frictional engagement of binding surfaces 68 with needle cannula 4. This configuration maintains needle cannula 4 within body base 54 to avoid hazardous exposure to distal end 104.

Aperture 66 is formed within aperture plate 65 for slidable engagement with needle cannula 4 during movement between the retracted position and the extended position of body base 54. Aperture 66 includes binding surfaces 68 formed on opposing sides of aperture 66 that engage needle cannula 4 to prevent movement thereof in the extended position of body base 54. It is contemplated that engagement to prevent movement of needle cannula 4 may include penetrating, frictional, interference, etc. It is envisioned that aperture 66 may have various geometric configurations, such as radial, polygonal, etc. It is further envisioned that aperture 66 may define an open cavity within aperture plate 65, such as, for example, "U" shaped and open to one or a plurality of edges of aperture plate 65.

The inclination of aperture plate 65 relative to longitudinal axis x facilitates sliding and binding, via binding surfaces 68, of needle cannula 4 within body base 54 to prevent hazardous exposure to distal end 104. For example, as shown in FIG. 6, aperture plate 65 is oriented at an angle of approximately 90° relative to longitudinal axis x such that aperture plate 65 is disposed substantially perpendicular to needle cannula 4. In this sliding orientation, needle cannula 4 is free to slide within aperture 66. As needle cannula 4 is retracted and body base 54 is extended, needle cannula 4 continues to engage needle communicating surface 72 and aperture plate 65 maintains its perpendicular orientation relative to longitudinal axis x.

As body base 54 is manipulated to the extended position, friction members 62 in conjunction with blocking member 116, 118 cause aperture plate 65 to rotate counterclockwise relative to longitudinal axis x. As shown in FIG. 26, aperture plate 65 rotates out of perpendicular alignment with needle cannula 4 such that aperture plate 65 is oriented at an angle α, which is less than 90° with respect to longitudinal axis x. It is contemplated that angle α may be measured from either side of aperture plate 65. Aperture plate 65 rotates to angle α and binding member 40 approaches the binding orientation.

For example, as shown in FIG. 1, body base 54 is in the retracted position and needle cannula 4 is fully extended. Binding member 40 and aperture plate 65 are in a sliding orientation such that aperture plate 65 is substantially perpendicular to longitudinal axis x. Blocking members 116, 118 may engage aperture plate 65 to maintain aperture plate 65 in the perpendicular orientation. Blocking members 116, 118 may also maintain such orientation during extension of needle cannula 4 or may not engage needle cannula 4.

As needle cannula 4 is retracted and body base 54 is manipulated to the extended position (FIG. 33), friction members 62 create a drag force via engagement with needle cannula 4 on binding member 40 and in conjunction with blocking member 118 cause aperture plate 65 to rotate in a counter-clockwise direction to the binding orientation. Blocking member surface 118A engages aperture plate 65 to facilitate rotation thereof from the perpendicular position into the binding orientation such that binding surfaces 68 engage needle cannula 4 to prevent axial movement thereof relative to body base 54 in the extended position. This configuration advantageously prevents hazardous exposure to needle cannula 4.

It is contemplated that binding surfaces 68 may include sharp edges to increase frictional engagement. It is further contemplated that the binding friction force may be created and varied by one or more altering factors, such as, for example, aperture 66 configuration and dimension, needle cannula 4 configuration and dimension, aperture plate 65 thickness, the dimension from blocking members 116, 118 contact point to the centerline of needle cannula 4 and the coefficient of friction between aperture 66 and needle cannula 4 depending on the particular requirements of a needle application. It is envisioned that friction members 62 may be configured to vary the drag force with variation of the inclination of aperture plate 65, which may be accomplished by geometric changes in the shape of friction members 62, such as wedge shapes or the inclusion of notches to engage needle cannula 4, or through the selective application of friction modifying materials or coatings such as oils, jells, greases, or coatings which increase friction. It is further envisioned that aperture 66 may be formed to accomplish the function of friction members 62.

In operation, medical needle shield apparatus 100, similar to that described in accordance with the principles of the present disclosure is provided for a tissue biopsy procedure. The components of medical needle shield apparatus 100 are fabricated, properly sterilized and otherwise prepared for storage, shipment and use. Referring to FIG. 1, medical needle shield apparatus 100 is in the primary state such that needle cannula 4 is fully extended to enclose recess 1 of stylette 2 and the actuating mechanism is not in a triggered condition. Medical needle shield apparatus 100 is manipulated via handle 26.

Initially, the actuating mechanism is set by manipulating trigger-setting button 12 in a proximal direction to retract needle cannula 4 and stylette 2, and compress spring 6, as discussed. Body 50 is manipulated such that distal end 104 of needle cannula 4 is inserted into the tissue of a subject (not shown) for biopsy sampling. Proper positioning of distal end 104 in the tissue may be verified by echogenic features and depth markings 108. It is contemplated that positioning of distal end 104 or guidance thereof may be facilitated by imaging devices, such as, for example, radiological, ultrasound, etc.

Stylette 2 is advanced into the tissue to be sampled by manually urging trigger-setting button 12 in the distal direction. Advancement of stylette 2 exposes stylette recess 1. The tissue to be sampled then prolapses into stylette recess 1. Upon full depression of trigger-setting button 12, the actuating mechanism expands spring 6 and needle cannula 4 is released. Spring 6 drives needle cannula 4 distally. Distal end 104 of needle cannula 4 cuts and captures the tissue prolapsed into stylette recess 1.

Medical needle shield apparatus 100 is withdrawn from the subject. The actuating mechanism is set, as described, and stylette 2 is manually advanced exposing the tissue sample. The sample is caused to exit stylette recess 1 into a receptacle or the like. Tissue sampling employing medical needle shield apparatus 100 may be repeated as desired. Other methods of use are also contemplated.

Figure 33:
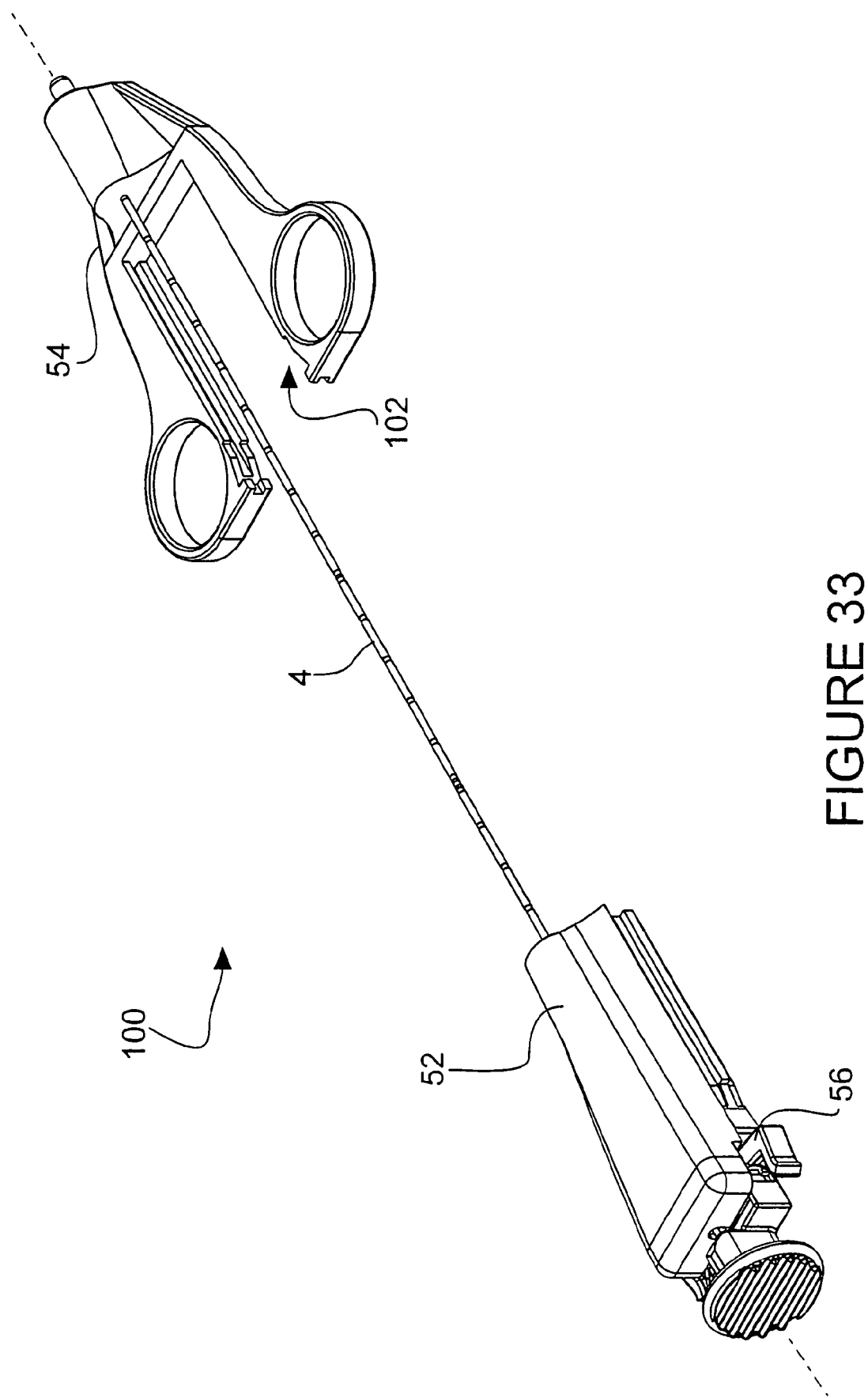
FIG. 33 is a perspective view of the medical needle shield apparatus shown in FIG. 1 with parts separated.

During the tissue biopsy sampling procedure, body base 54 is in the retracted position and needle cannula 4 is extended, as shown in FIG. 1. Binding member 40 is in a sliding orientation and needle cannula 4 may freely slide, as discussed. Upon completion of the tissue biopsy sampling procedure, distal end 104 is protected to prevent hazardous exposure thereto. Needle cannula 4 is retracted and body base 54 is manipulated to the extended position (FIG. 33). Binding member 40 rotates to the binding orientation, as discussed, to prevent axial movement of needle cannula 4 while distal end 104 is safely disposed within body base 54 to advantageously prevent hazardous exposure to needle cannula 4.

In an alternate embodiment, as shown in FIGS. 34–62, medical needle shield apparatus 100 has a body 50 that includes a first housing, such as, for example, body core 52. Body core 52 includes base handle 26. Body core 52 also includes an actuating mechanism that actuates a needle cannula 4 disposed therewith. The actuating mechanism, as previously described, advances needle cannula 4 to facilitate tissue sampling. An inner needle, such as, for example, stylette 2 is disposed for slidable movement within needle cannula 4. Needle cannula 4 is concentric with stylette 2. Stylette 2 has a recess 1 configured to capture tissue samples, as previously discussed.

Stylette 2 is fixed to the trigger-setting button 12, while being held concentric to the stylette 2 via bushing 8. The interaction between the trigger-setting button 12 and coring cannula slide 10 is accomplished by spring 6 and base handle 26. The spring 6 resides concentric to stylette 2, saddled over bushing 8, and against the proximal side of the coring cannula slide 10. The trigger-setting button 12 is supported by the base handle 26, so as to allow only axial motion of the stylette 2 within needle cannula 4. Trigger-setting arm 14 includes a trigger-setting tooth 16, which is configured for disposal within a groove 105 of coring cannula slide 10.

Figure 34:
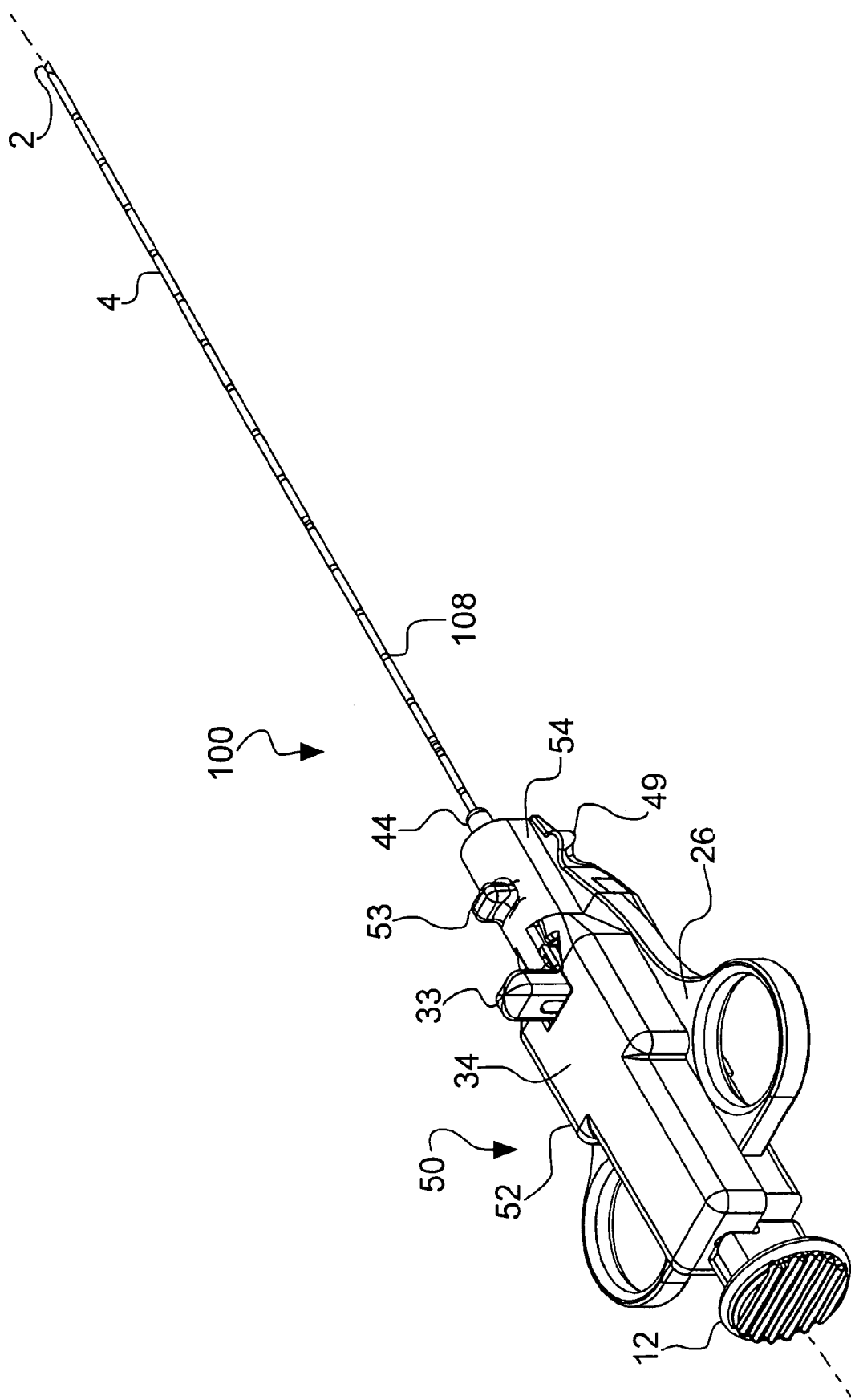
FIG. 34 is a perspective view of another embodiment of a medical needle shield apparatus in accordance with the principles of the present disclosure.
Figure 35:
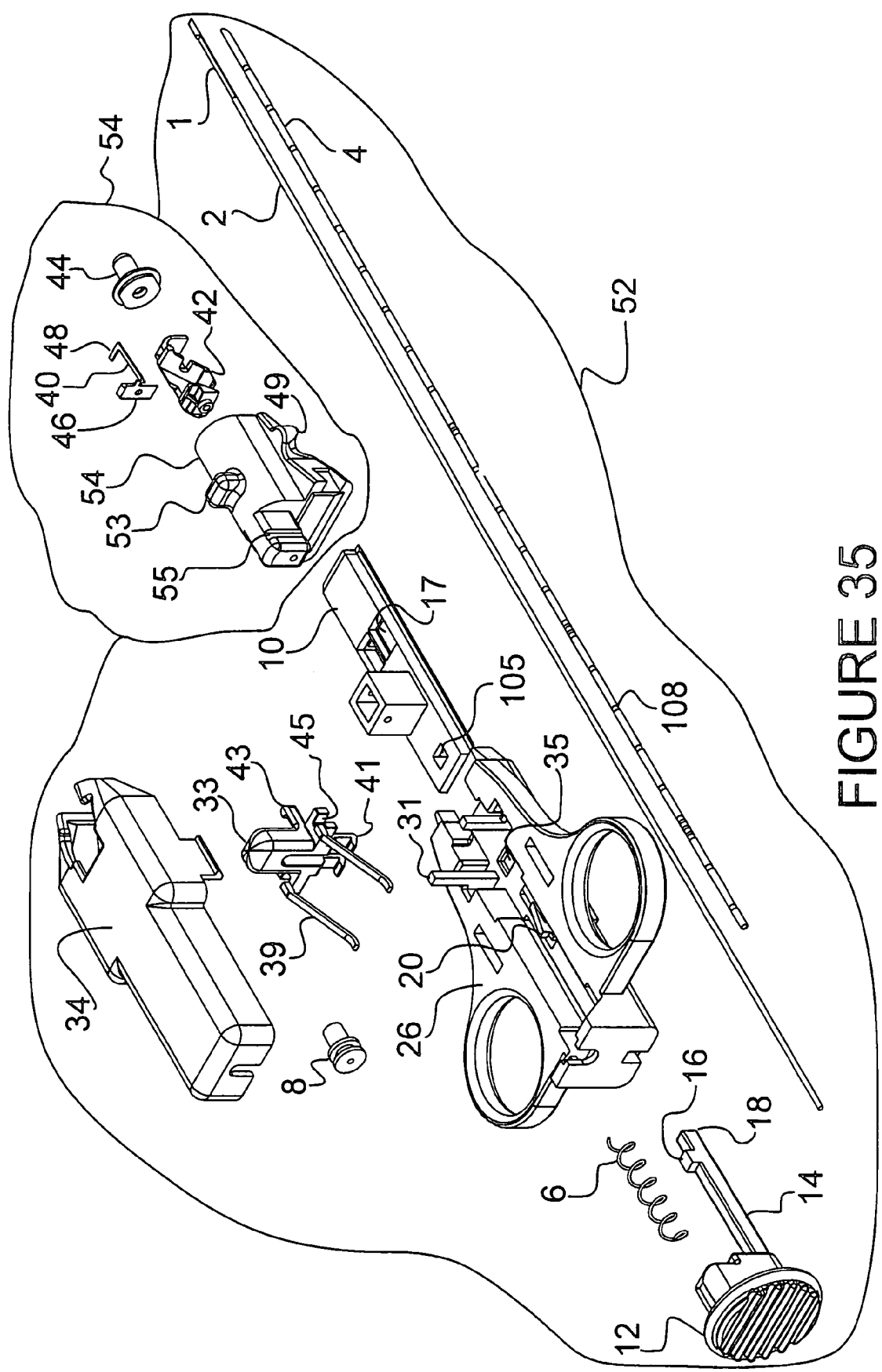
FIG. 35 is a perspective view of the medical needle shield apparatus shown in FIG. 34 with parts separated.
Figure 36:
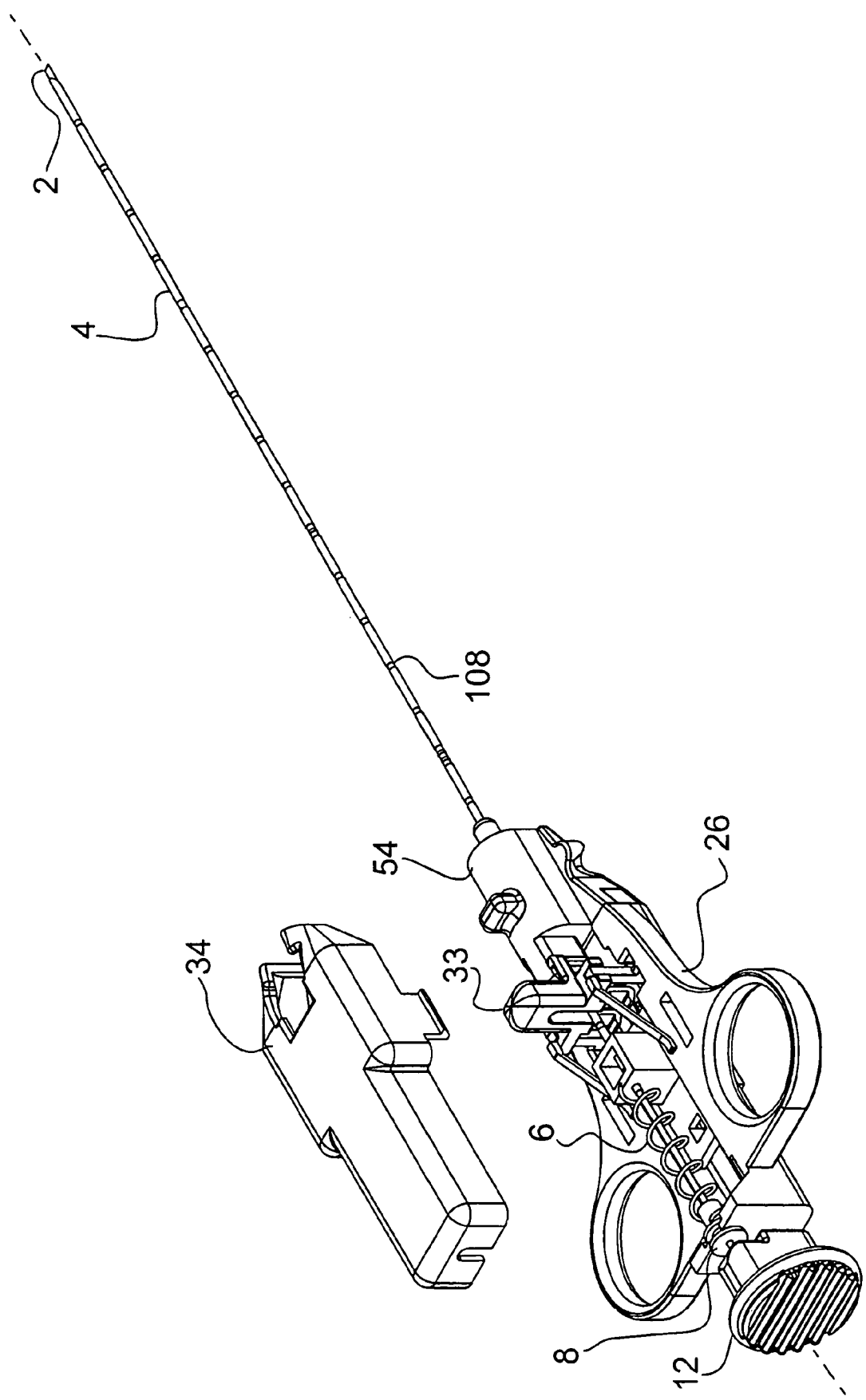
FIG. 36 is a cutaway perspective view of the medical needle shield apparatus shown in FIG. 34 with a housing section removed.

In a primary state of medical needle shield apparatus 100, as shown in FIGS. 34, 36 and 37, spring 6 is expanded and trigger-setting button 12 and coring cannula slide 10 are in a distal position on base handle 26. Needle cannula 4 and stylette 2 are attached to coring cannula slide 10 and trigger-setting button 12, respectively, each in a distal position. In such a distal position, recess 1 of stylette 2 is enclosed by needle cannula 4, as shown in FIG. 37. Binding member 40 is in a non-binding or sliding orientation, as will be discussed, which allows needle cannula 4 to slide freely.

To set the actuating mechanism, trigger-setting button 12 is manipulated in a proximal direction along longitudinal axis x, in the direction of arrow A shown in FIGS. 39 and 41. Needle cannula 4 maintains enclosure of recess 1 of stylette 2, as shown in FIG. 40. Trigger-setting arm 14 includes a trigger-setting tooth 16, which is configured for disposal within a groove 105 of coring cannula slide 10. Disposal of trigger-setting tooth 16 within groove 105 causes corresponding engagement with proximal slide stop 9, as shown in FIG. 45. Correspondingly, a distal slide stop 11 of coring cannula slide 10 engages a compression lock 20, as shown in FIG. 44. Proximal slide stop 9 and distal slide stop 11 thereby facilitate maintenance of the actuating mechanism in a set position. Proximal movement of trigger-setting button 12 also compresses spring 6 into a set position. In the set position, needle cannula 4 maintains enclosure of recess 1 of stylette 2, as shown in FIG. 42. A button 33 and button locking tooth 41 are held above the slide action by a button spring return 39, which allows the coring cannula slide 10 to slide without interference.

Figure 48:
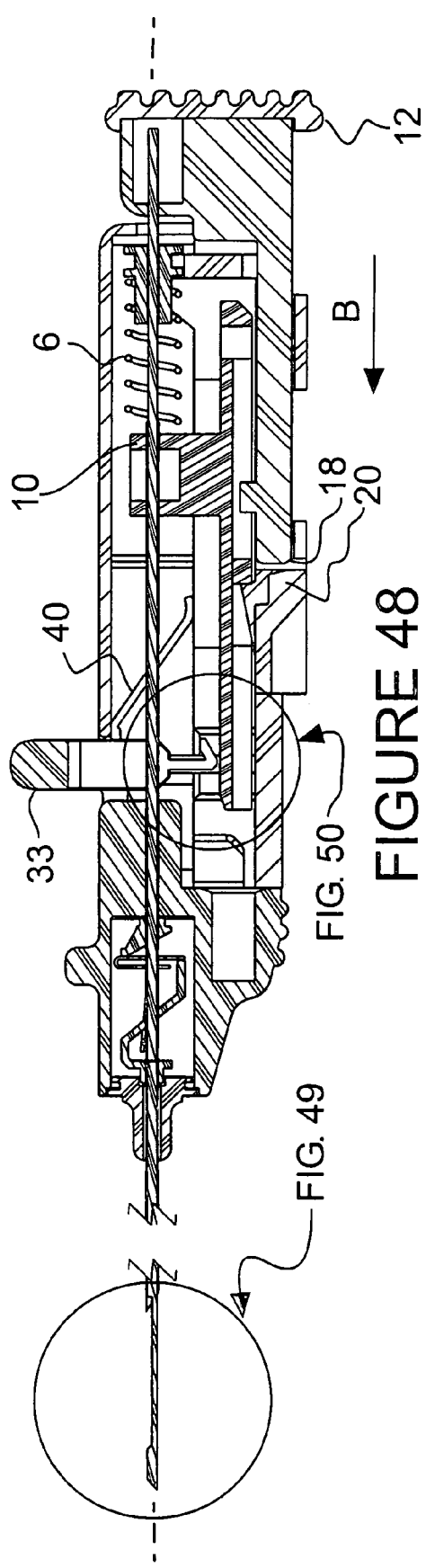
FIG. 48 is a cutaway cross-sectional view of the medical needle shield apparatus shown in FIG. 34.
Figure 50:
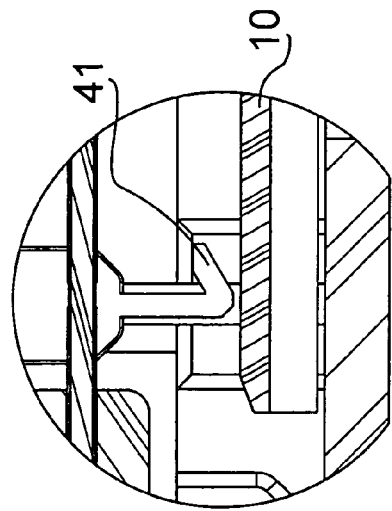
FIG. 50 is a cross-sectional view of the indicated area of detail shown in FIG. 48.
Figure 49:
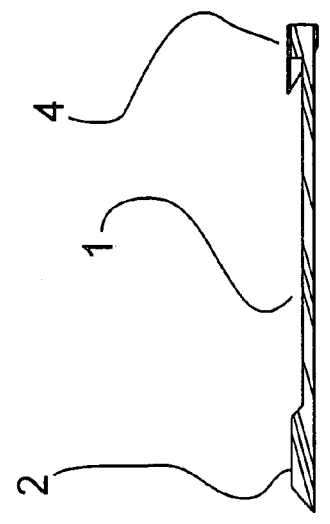
FIG. 49 is a cross-sectional view of the indicated area of detail shown in FIG. 48.

In contemplation of actuation of needle cannula 4, trigger-setting button 12 is manipulated in a distal direction, as shown by arrow B in FIGS. 46 and 48, until resistance is encountered. For example, a source of resistance to the distal manipulation can include engagement of a distal slide stop 11 with compression lock 20, as shown in FIG. 44. The distal manipulation of trigger-setting button 12 forces stylette 1 forward and exposes recess 1, as shown in FIGS. 47 and 49, while spring 6 is maintained in compression. Button spring return 39 maintains button 33 and button locking tooth 41 above the slide action, as shown in FIG. 50.

Figure 52:
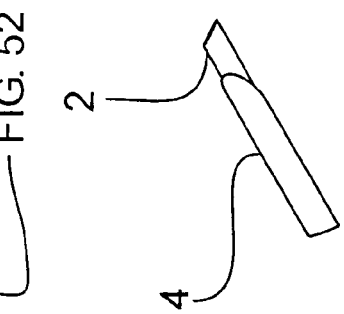
FIG. 52 is a perspective view of the indicated area of detail shown in FIG. 51.

In an exemplary actuation, needle cannula 4 and stylette 2 are placed through soft tissue of a subject (not shown) to a desired location, which may be viewed via echogenic and depth markings 108. At the desired location, a tissue sample for biopsy enters recess 1. Trigger-setting button 12 is manipulated distally beyond the initial resistance of trigger core activating ramp 18 with compression lock 20, as shown by arrow C in FIG. 53. Further manipulation of button 12 drives trigger core activating ramp 18 to deflect compression lock 20 such that distal slide stop 11 disengages from compression lock 20, as shown by arrow CC in FIG. 54. Thus, coring cannula slide 10 is thrust, via spring 6, to a distal position, as shown by arrow D in FIG. 51. Correspondingly, needle cannula 4 is thrust distally to core and enclose the soft tissue within recess 1, as shown in FIGS. 52 and 53. The captured soft tissue sample is then withdrawn from the subject. The captured soft tissue sample is removed by resetting the actuating mechanism and distally manipulating button 12 to expose recess 1, as described above, outside of the subject. Additional soft tissue sampling may be repeated with medical needle shield apparatus 100.

Figure 51:
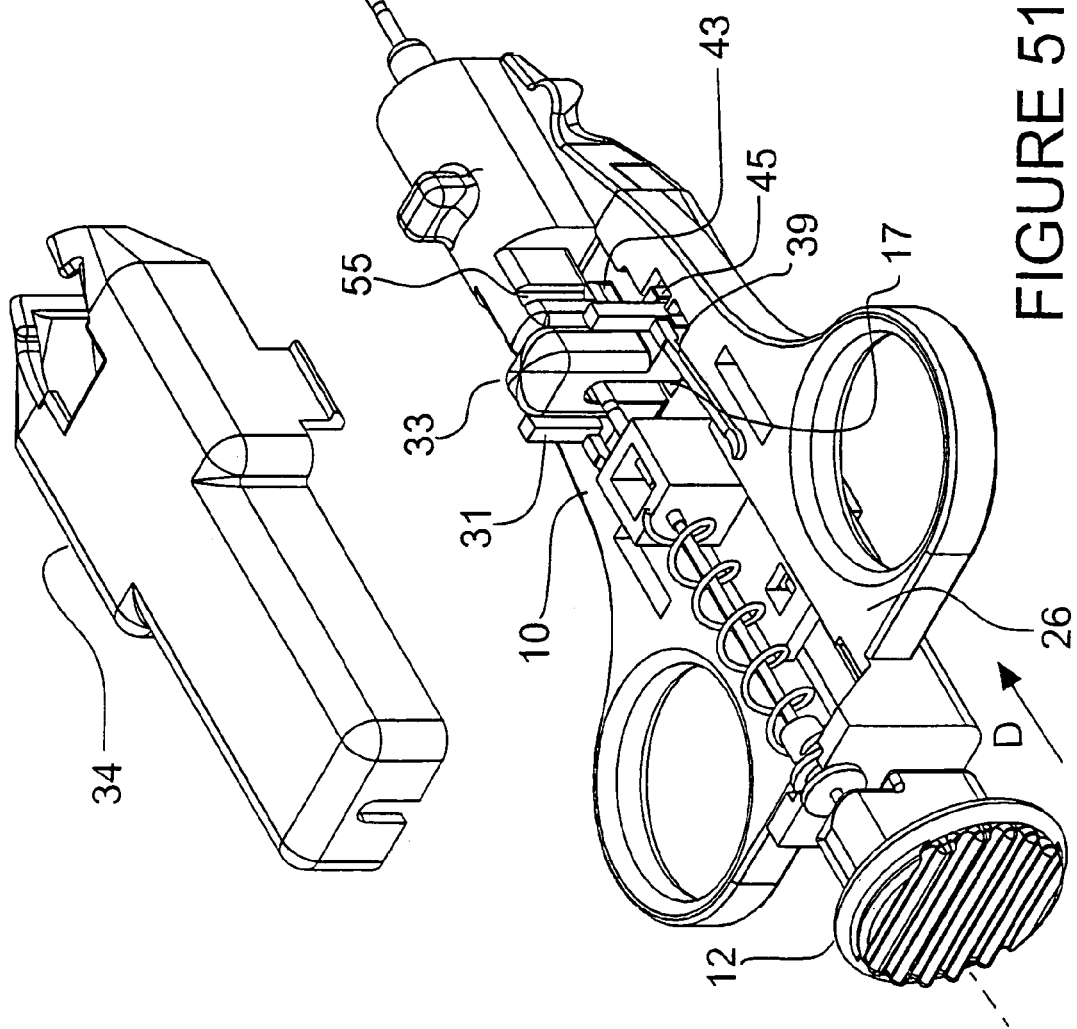
FIG. 51 is a cutaway perspective view of the medical needle shield apparatus shown in FIG. 34 with a housing section removed.

Body base 54 remains adjacent to body core 52 by means of a pre-activation locking channel 55, while attached to the pre-activation locking arm 43 of button 33. After soft tissue core samples are harvested, the medical needle shield apparatus 100 may readied for activation by fully depressing button 33 until it is flush with base cover 34. Button 33 may then slide vertically along button guide channel 45 interface with base guide rails 31, as shown in FIG. 51. This action locks out coring cannula slide 10. Button locking tooth 41 slides through the slide lockout gap 17 and base lockout gap 35. It is contemplated that slide lockout gap 17 may be located at various positions along coring cannula slide 10. Button locking tooth 41 then engages the edge of base handle 26, which disables the pre-setting of and triggering of coring cannula slide 10, as shown in FIGS. 57 and 58. It is contemplated that the orientation of button locking tooth 41 may be varied.

Button 33 can only be depressed when the medical needle shield apparatus 100 is in its primary state. Slide lockout gap 17 assists as a physical verification when in line with button locking tooth 41. Consequently, button 33 may only be depressed when coring cannula slide 10 is in its primary state. If button 33 is depressed when the medical needle shield apparatus 100 is in any other state, button locking tooth 41 contacts the flat surface of coring cannula slide 10 and will not lock out.

Figure 59:
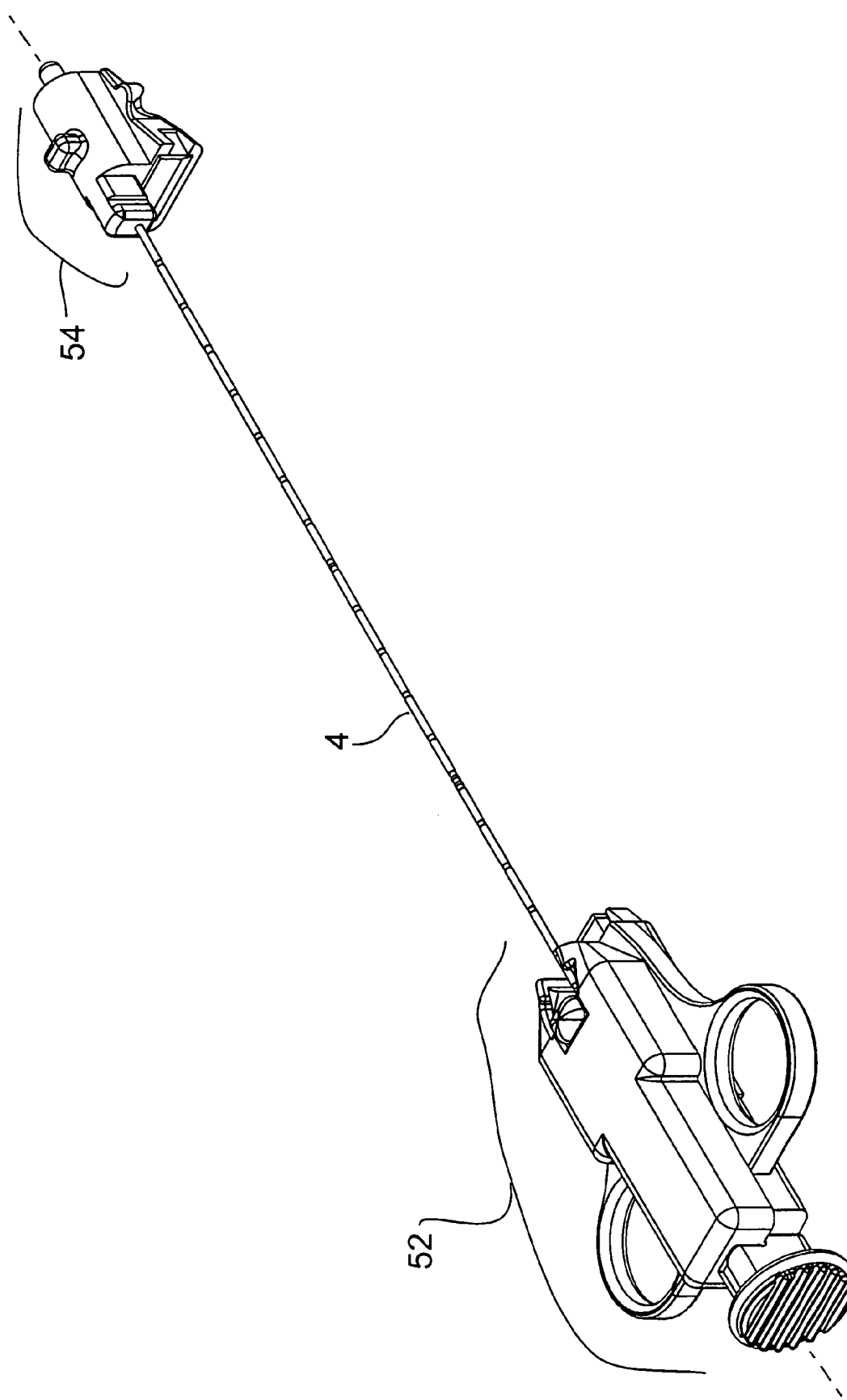
FIG. 59 is a cutaway perspective view of the medical needle shield apparatus shown in FIG. 34 with parts separated.
Figure 60:
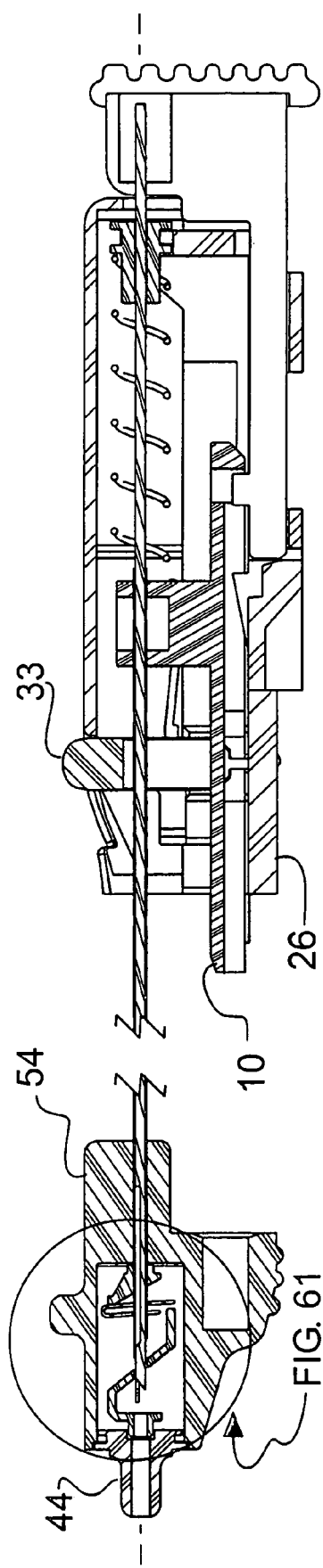
FIG. 60 is a cutaway cross-sectional view of the medical needle shield apparatus shown in FIG. 34 with parts separated.
Figure 61:
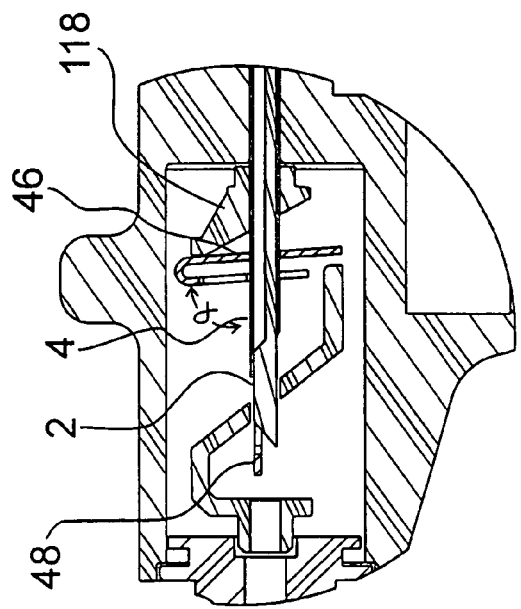
FIG. 61 is a cross-sectional view of the indicated area of detail shown in FIG. 60.

As the coring cannula slide 10 is locked out, base 54 is disengaged from body core 52 as pre-activation locking arms 43 slide past pre-activation locking channel 55, as shown in FIGS. 57–59. Base 54 is then extensible from a retracted position (FIG. 34) to an extended position (FIG. 59) to enclose a sharp distal end 104 of needle cannula 4. Base 54 may be gripped by means of thumb grip 53 or side grips 49. In the extended position, a binding member 40 disposed in base 54 binds to the needle cannula 4 as end-sensing member 48 detects the distal end of stylette 2 (FIGS. 60–61), as previously described.

Figure 62:
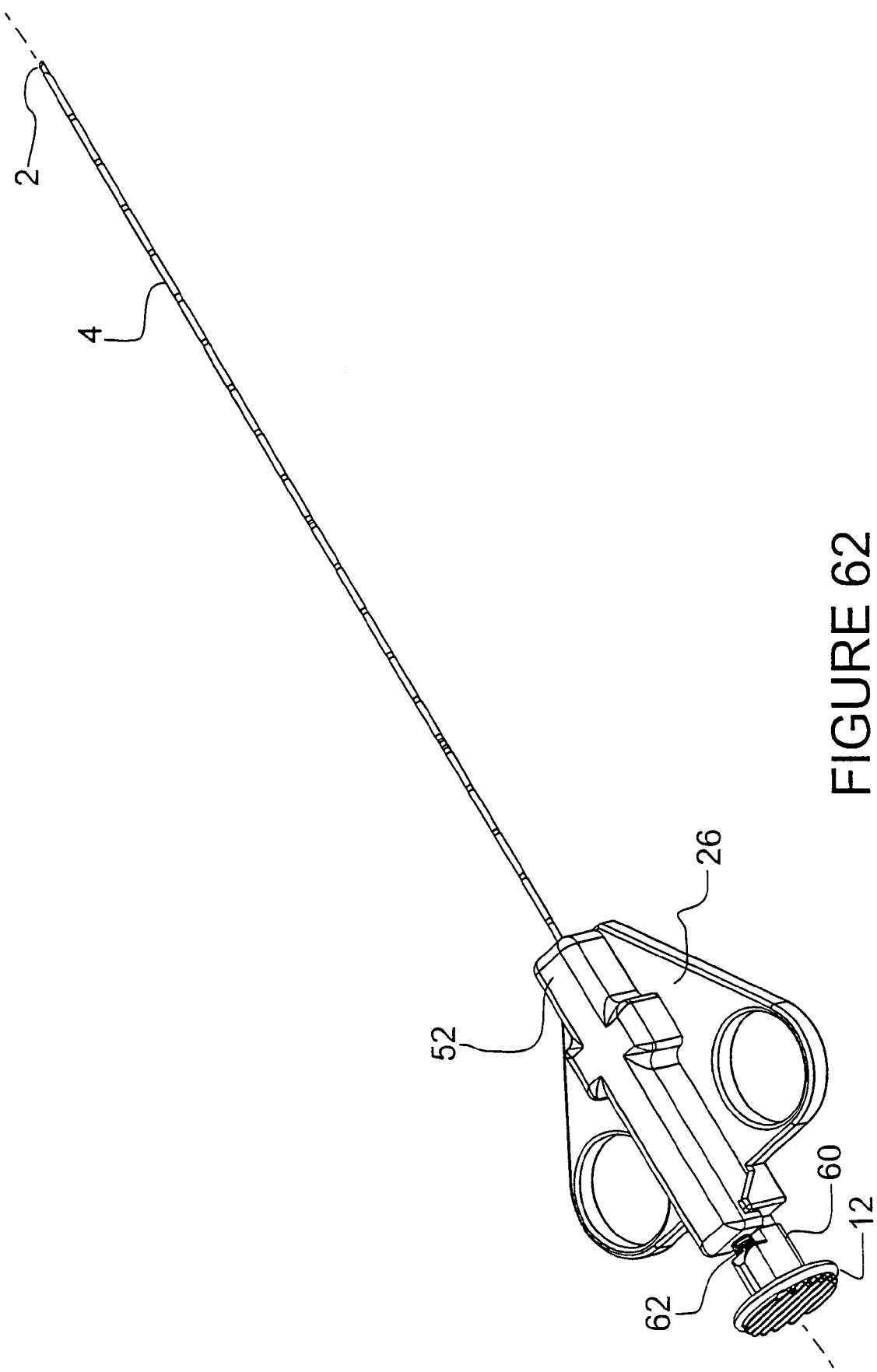
FIG. 62 is a perspective view of another embodiment of a medical needle shield apparatus in accordance with the principles of the present disclosure.
Figure 63:
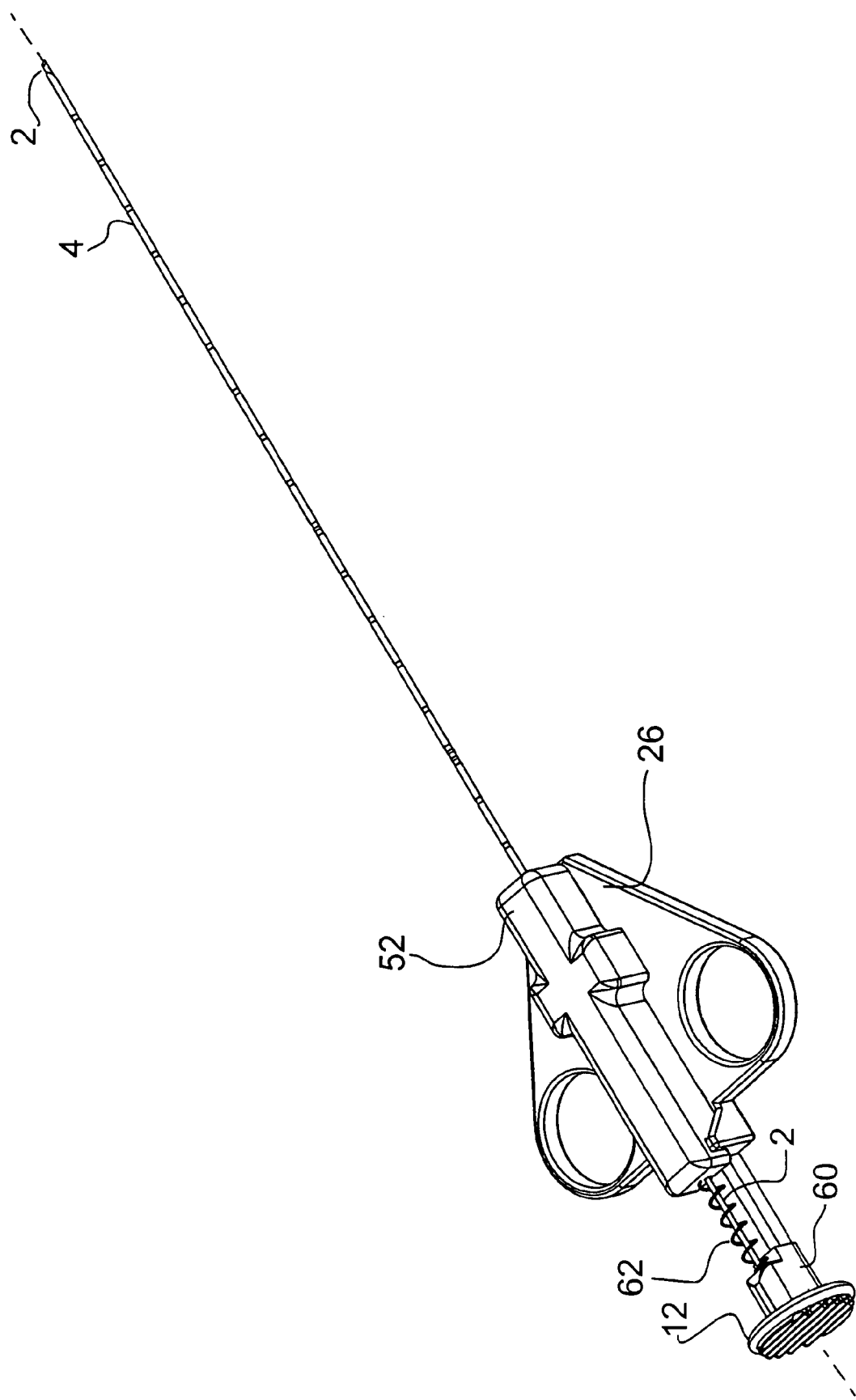
FIG. 63 is perspective view of the apparatus shown in FIG. 62 in an alternate position.
Figure 64:
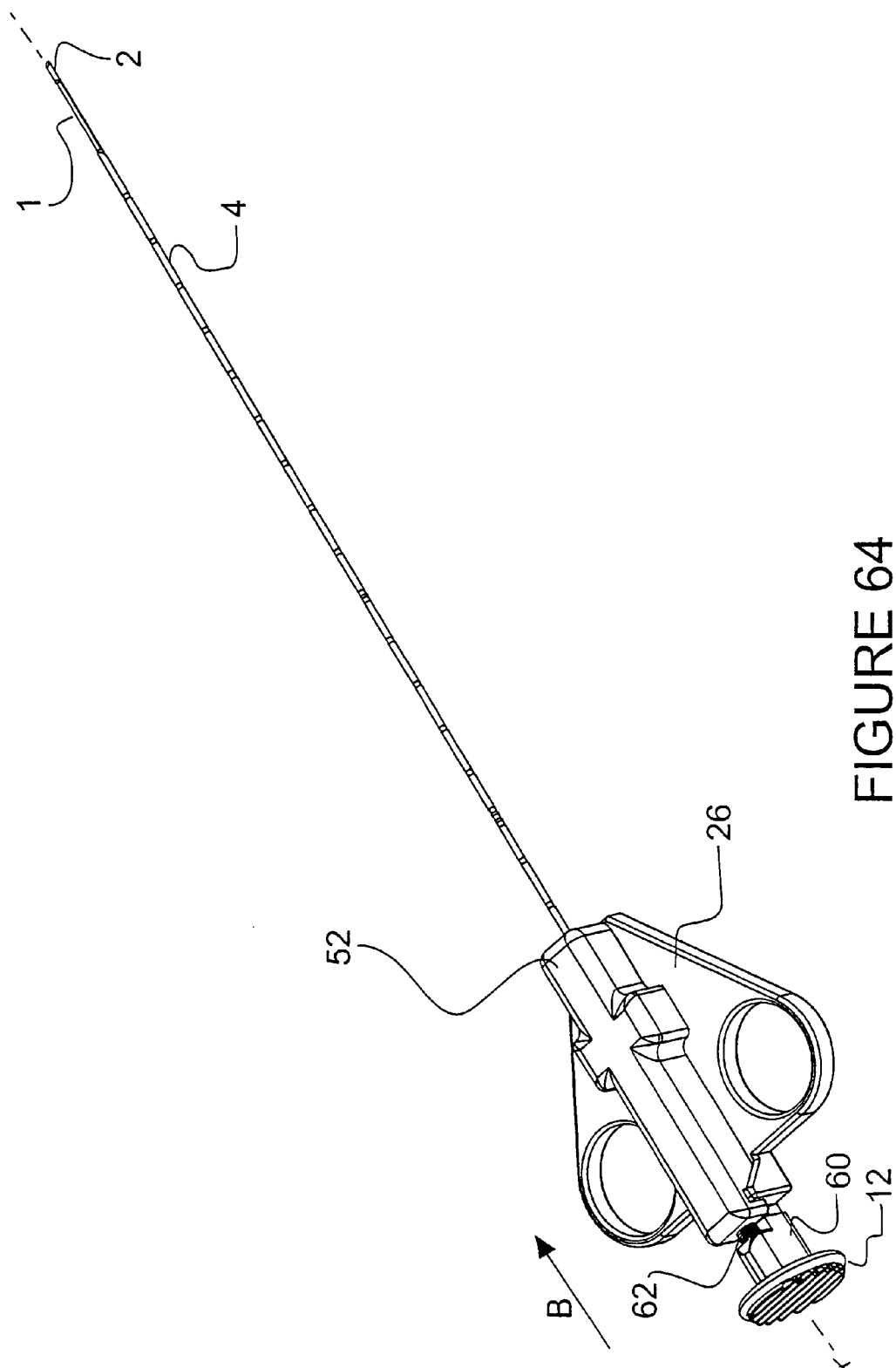
FIG. 64 is a perspective view of the apparatus shown in FIG. 62 in an alternate position.

In an alternate embodiment, as shown in FIGS. 62–64, an energy storing component, such as spring 62, may be utilized to maintain the biopsy instrument in a pre-activated condition. In the pre-activated condition, the stylette 2 is covered by cannula 4 (FIG. 62). As trigger-setting arm 60 is set, spring 62 is in a compressed state and holds trigger-setting button 12 and trigger-setting arm 60 in a proximal position.

Energy storing component, such as spring 62, may be utilized to maintain the biopsy instrument in a pre-activated condition. In the pre-activated condition, the stylette 2 is covered by cannula 4 (FIG. 63). As trigger-setting arm 60 is set, spring 62 is in an extended state and holds trigger-setting button 12 and trigger-setting arm 60 in a proximal position. Without spring 62, stylette 2 is free to slide forward.

An external force in the direction of arrow B is required in the process of advancing stylette 2 to expose stylette recess 1 in a core harvesting function or in releasing a previously harvested core sample (FIG. 64). This external force must overcome the opposing force generated by spring 62 to advance stylette 2 in either function (FIG. 64). As stylette 2 requires repositioning within a specimen or as a previously harvested core sample has been disposed of, an operator then removes the external force applied to trigger-setting button 12. Stylette 2 then automatically withdraws inside needle cannula 4, thereby covering stylette recess 1 as shown in FIG. 63. An operator is then able to harvest an additional core sample or to readjust within a tissue without manually drawing stylette 2 to its most proximal position. An added benefit is that spring 62 positions stylette 2 and/or trigger-setting arm 60 in a proximal position to lock out the gun portion of the instrument and prevent stylette 2 and/or trigger-setting arm 60 to from advancing once locked out.

The invention of the present disclosure may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A medical needle shield apparatus comprising:
   a first housing being configured to actuate a needle cannula disposed therewith; and
   a second housing being releasably engageable with the first housing, the needle cannula being disposed for slidable movement with the second housing such that the second housing is extensible from a retracted position to an extended position to enclose a distal end of the needle cannula;
   a binding member disposed within the second housing and comprising binding surfaces that define an aperture configured for slidable receipt of the needle cannula between the retracted position and the extended position,
   the binding member further comprising a retainer extending therefrom such that the retainer is engageable with the needle cannula to prevent inclination of the binding member while the retainer is engaged with the needle cannula,
   the binding member further comprising one or more drag inducing members that engage the needle cannula during slidable receipt of the needle cannula to create a drag force with the needle cannula, the drag force and second housing facilitating inclination of the binding member relative to a longitudinal axis of the needle cannula once the retainer extends beyond the distal end of the needle cannula such that the binding surfaces engage the needle cannula to prevent slidable movement of the needle cannula in the extended position of the second housing.

2. A medical needle shield apparatus as recited in claim 1, wherein the binding member includes a substantially planar aperture plate that includes the binding surfaces that form the aperture.

3. A medical needle shield apparatus as recited in claim 2, wherein the one or more drag inducing member includes a pair of arms extending from the aperture plate.

4. A medical needle shield apparatus as recited in claim 1, wherein the second housing includes an inner housing that is disposed with the binding member.

5. A medical needle shield apparatus as recited in claim 4, wherein the inner housing defines one or more blocking members extending from an interior surface thereof, the one or more blocking members being engageable with the binding member for urging the binding member to a binding orientation.

6. A medical needle shield apparatus as recited in claim 1, wherein the needle cannula includes an inner needle disposed for slidable movement with the needle cannula.

7. A medical needle shield apparatus as recited in claim 6, wherein the inner needle includes a lateral recess disposed adjacent a distal end thereof.

8. A medical needle shield apparatus as recited in claim 6, further including a means for selectively locking movement between the needle cannula and inner needle.

9. A medical needle shield apparatus as recited in claim 6, wherein the inner needle includes a cutting edge.

10. A medical needle shield apparatus as recited in claim 1, wherein the needle cannula includes a cutting edge.

11. A medical needle shield apparatus as recited in claim 1, wherein the second housing includes a handle, the handle defining a cavity configured for receipt of the first housing such that the first housing is releasably engageable with the second housing.

12. A medical needle shield apparatus as recited in claim 1, wherein the first housing includes a handle.

13. A medical needle shield apparatus as recited in claim 1, wherein the first housing is releasably engageable with the second housing.

14. A medical needle shield apparatus as recited in claim 1, wherein the first housing is releasably engageable with the second housing by means of an operable release.

15. A medical needle shield apparatus as recited in claim 14, wherein activation of the operable release selectively locks movement between the needle cannula and inner needle.

16. A medical needle shield apparatus as recited in claim 1, wherein the first housing includes a locking configuration that mates with a groove of the second housing to facilitate releasable engagement of the first housing and the second housing.

17. A medical needle shield apparatus as recited in claim 1, wherein the first housing includes an actuating mechanism that actuates the needle cannula.

18. A medical needle shield apparatus as recited in claim 17, wherein the actuating mechanism includes a slide mounted with the needle cannula, the slide facilitating axial movement of the needle cannula.

19. A medical needle shield apparatus as recited in claim 18, wherein the actuating mechanism includes a biasing member that engages the slide to bias the needle cannula in a distal direction.

20. A medical needle shield apparatus as recited in claim 19, wherein the actuating mechanism includes a trigger that is connected to the biasing member for actuation thereof.

21. A medical needle shield apparatus as recited in claim 19, including a spring means for maintaining the actuating assembly in a proximal position.

22. A medical needle shield apparatus comprising:
   a first housing including an actuating mechanism that actuates a needle cannula disposed therewith; and
   a second housing including a handle, the handle defining a cavity configured for receipt of the first housing such that the first housing is releasably engageable with the second housing, the needle cannula being disposed for slidable movement with the second housing such that the second housing is extensible from a retracted position to an extended position to enclose a distal end of the needle cannula,
      a binding member disposed within the second housing and comprising binding surfaces that define an aperture configured for slidable receipt of the needle cannula between the retracted position and the extended position,
   the binding member further comprising a retainer extending therefrom such that the retainer is engageable with the needle cannula to prevent inclination of the binding member while the retainer is engaged with the needle cannula,
   the binding member further comprising one or more drag inducing member that engage the needle cannula during slidable receipt of the needle cannula to create a drag force with the needle cannula, the drag force facilitating inclination of the binding member relative to a longitudinal axis of the needle cannula once the retainer extends beyond the distal end of the needle cannula such that the binding surfaces engage the needle cannula to prevent slidable movement of the needle cannula in the extended position of the second housing.

23. A medical needle shield apparatus as recited in claim 22, wherein the one or more drag inducing members includes a pair of arms extending from the aperture plate.

24. A medical needle shield apparatus as recited in claim 22, wherein the second housing includes an inner housing that is disposed with the binding member, the inner housing defining one or more blocking members extending from an interior surface thereof, the one or more blocking member being engageable with the binding member for urging the binding member to a binding orientation.

25. A medical needle shield apparatus as recited in claim 22, wherein the first housing includes a locking configuration that mates with a groove of the second housing to facilitate releasable engagement of the first housing and the second housing.

26. A medical needle shield apparatus as recited in claim 22, wherein the actuating mechanism includes a spring biased slide mounted with the needle cannula, the slide facilitating axial movement of the needle cannula.

27. A medical needle shield apparatus comprising:
   a core including a spring biased actuating mechanism that actuates a needle cannula disposed therewith, the actuating mechanism having a slide that is mounted with the needle cannula to facilitate axial movement thereof, the needle cannula including an inner needle disposed for slidable movement with the needle cannula, the inner needle including a lateral recess disposed adjacent a distal end thereof; and a base including a handle, the handle defining a cavity configured for receipt of the first housing such that the first housing is releasably engageable with the second housing, the needle cannula being disposed for slidable movement with the second housing such that the second housing is extensible from a retracted position to an extended position to enclose a distal end of the needle cannula, the second housing further comprising an inner housing that supports a binding member, the binding member having an aperture plate, the aperture plate comprising binding surfaces that define an aperture configured for slidable receipt of the needle cannula between the retracted position and the extended position, the binding member further comprising a retainer extending therefrom such that the retainer is engageable with the needle cannula to prevent inclination of the binding member while the retainer is engaged with the needle cannula, the binding member including one or more friction members that engage the needle cannula during slidable receipt of the needle cannula to create a drag force with the needle cannula, the drag force facilitating inclination of the binding member relative to a longitudinal axis of the needle cannula once the retainer extends beyond the distal end of the needle cannula such that the binding surfaces engage the needle cannula to prevent slidable movement of the needle cannula in the extended position of the second housing.

* * * * *